(12) United States Patent
Kim

(10) Patent No.: US 8,454,522 B2
(45) Date of Patent: Jun. 4, 2013

(54) METHOD AND APPARATUS FOR ESTIMATING BLOOD PRESSURE

(75) Inventor: Jong Pal Kim, Seoul (KR)

(73) Assignee: Samsung Electronics Co., Ltd. (KR)

( * ) Notice: Subject to any disclaimer, the term of this patent is extended or adjusted under 35 U.S.C. 154(b) by 581 days.

(21) Appl. No.: 12/686,422

(22) Filed: Jan. 13, 2010

(65) Prior Publication Data

US 2010/0305457 A1 Dec. 2, 2010

(30) Foreign Application Priority Data

May 27, 2009 (KR) .................. 10-2009-0046507

(51) Int. Cl.
*A61B 5/02* (2006.01)
(52) U.S. Cl.
USPC ............ 600/485; 600/494; 600/496; 600/500
(58) Field of Classification Search
USPC .......................... 600/490–504, 483–485, 481
See application file for complete search history.

(56) References Cited

U.S. PATENT DOCUMENTS

| | | | |
|---|---|---|---|
| 6,371,921 B1 * | 4/2002 | Caro et al. | 600/485 |
| 7,951,086 B2 * | 5/2011 | Flaherty et al. | 600/485 |
| 2006/0004293 A1 | 1/2006 | Flaherty et al. | |
| 2010/0274143 A1 * | 10/2010 | Kim et al. | 600/493 |

FOREIGN PATENT DOCUMENTS

| | | |
|---|---|---|
| JP | 11-318899 | 11/1999 |
| JP | 2002-224065 | 8/2002 |
| JP | 2003-305013 | 10/2003 |
| JP | 2004-195204 | 7/2004 |
| KR | 10-2006-0004293 | 1/2006 |
| KR | 10-2006-0123339 | 12/2006 |
| KR | 10-2008-0086300 | 9/2008 |

* cited by examiner

*Primary Examiner* — Michael Kahelin
*Assistant Examiner* — Mitchell Alter
(74) *Attorney, Agent, or Firm* — Cantor Colburn LLP

(57) ABSTRACT

A method for estimating blood pressure includes sensing a sphygmus wave at a body part of a user to which vibration is applied to generate a sensed sphygmus wave, filtering the sensed sphygmus wave to generated a filtered sphygmus wave, and estimating blood pressure of the user based on time differences between peaks of the sensed sphygmus wave and peaks of the filtered sphygmus wave.

20 Claims, 19 Drawing Sheets

METHOD AND APPARATUS FOR ESTIMATING BLOOD PRESSURE

CROSS-REFERENCE TO RELATED APPLICATION

This application claims priority to Korean Patent Application No. 10-2009-0046507, filed on May 27, 2009, and all the benefits accruing therefrom under 35 U.S.C. §119, the content of which in its entirety is herein incorporated by reference.

BACKGROUND

1) Field

The general inventive concept relates to an apparatus for estimating blood pressure, and a method for the same.

2) Description of the Related Art

Blood pressure is often used as an index of a person's general health condition. As a result, apparatuses for measuring blood pressure are commonly used in both medical institutions and at home. The U.S. Food and Drug Administration ("FDA") promulgates standards for these apparatuses for measuring blood pressure, such that the apparatuses comply with the requirements of the U.S. Association for the Advancement of Medical Instrumentation ("AAMI"). In addition, the American National Standards Institute ("ANSI")/AAMI SP10, issued by the AAMI, includes specific details related to the apparatuses, such as safety and performance requirements therefor.

A blood pressure measurement typically includes a systolic blood pressure, which is a pressure when an initial pulse sound is heard while a pressure applied to a site where arterial blood flows is slowly reduced (after the pressure is applied to stop blood flow in the artery), as well as a diastolic blood pressure, which is a pressure corresponding to when no pulse sound is heard after the pressure is further reduced.

More specifically, for example, a digital hemadynamometer, which is one type of apparatus for measuring blood pressure, calculates blood pressure by detecting a waveform corresponding to a pressure measured while pressure is applied to a blood vessel.

SUMMARY

The general inventive concept includes a method and apparatus for estimating blood pressure, without using a characteristic ratio statistically obtained via experimentation. Also provided is a computer readable recording medium having recorded thereon a computer program for executing the method.

A blood pressure estimating method includes: sensing a sphygmus wave at a body part of a user to which vibration is applied to generate a sensed sphygmus wave; filtering the sensed sphygmus wave to generate a filtered sphygmus wave; and estimating blood pressure of the user based on time differences between peaks of the sensed sphygmus wave and peaks of the filtered sphygmus wave.

A computer program product includes a computer readable computer program code for executing a method of estimating blood pressure and instructions for causing a computer to implement the method, the method including: sensing a sphygmus wave at a body part of a user to which vibration is applied to generate a sensed sphygmus wave; filtering the sensed sphygmus wave to generate a filtered sphygmus wave; and estimating blood pressure of the user based on time differences between peaks of the sensed sphygmus wave peaks of the filtered sphygmus wave.

A blood pressure estimating apparatus includes: a sensing unit which senses a sphygmus wave at a body part of a user to which vibration is applied to generate a sensed sphygmus wave; a filtering unit which filters the sensed sphygmus wave to generate a filtered sphygmus wave; a blood pressure estimation unit which estimates blood pressure of the user based on time differences between peaks of the sensed sphygmus wave and peaks of the filtered sphygmus wave; and a user interface unit which outputs estimated blood pressures.

BRIEF DESCRIPTION OF THE DRAWINGS

The above and/or other aspects will become more readily apparent and appreciated from the following description of embodiments thereof, taken in conjunction with the accompanying drawings, in which.

DETAILED DESCRIPTION

Figure 1:
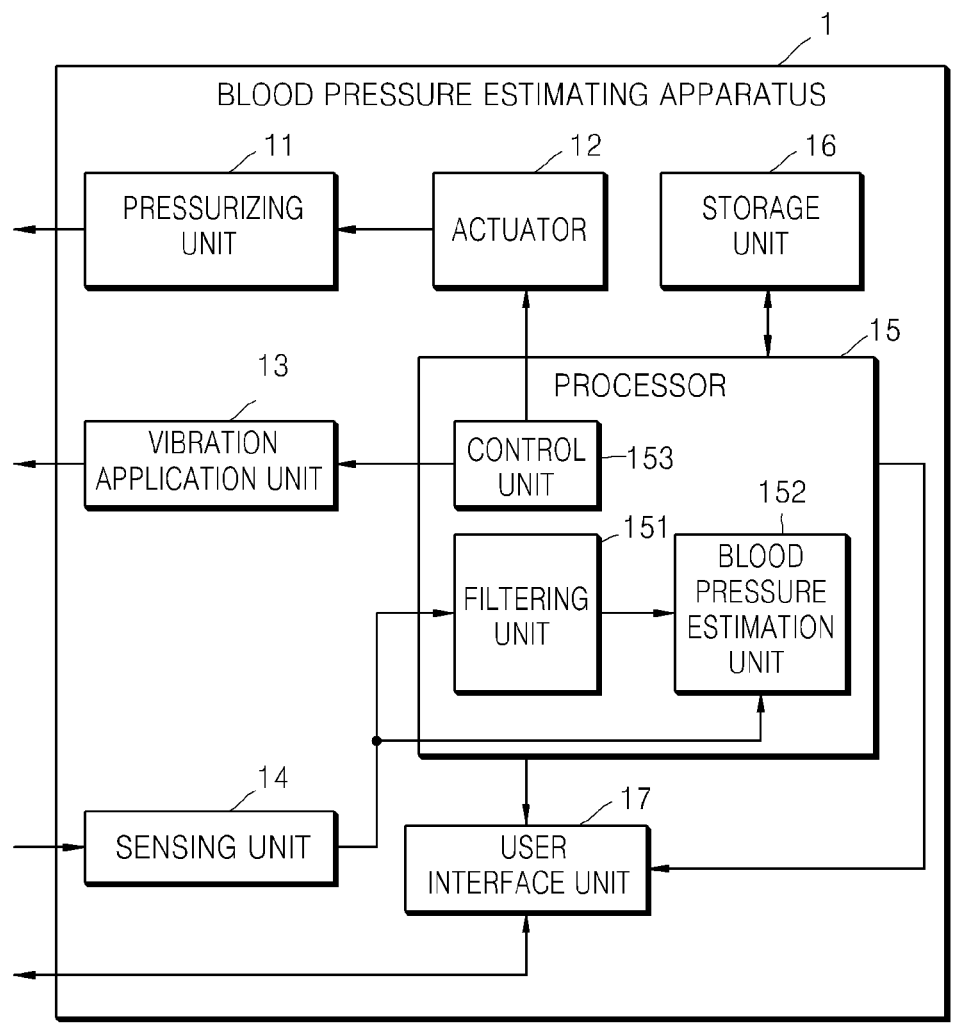
FIG. 1 is a block diagram illustrating a blood pressure estimating apparatus according to an embodiment.

The general inventive concept now will be described more fully hereinafter with reference to the accompanying drawings, in which various embodiments are shown. The general inventive concept may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Hereinafter, embodiments of the general inventive concept will be described in further detail with reference to the accompanying drawings.

FIG. 1 is a block diagram illustrating a blood pressure estimating apparatus 1 according to an embodiment. Referring to FIG. 1, the blood pressure estimating apparatus 1 includes a pressurizing unit 11, an actuator 12, a vibration application unit 13, a sensing unit 14, a processor 15, a storage unit 16 and a user interface unit 17. The processor 15 includes a filtering unit 151, a blood pressure estimation unit 152 and a control unit 153. The processor 15 may include an array of logic gates, and/or a combination of a specific- or general-use microprocessor and a memory which stores a program to be executed in the specific- or general-use microprocessor. It will be noted that, in additional embodiments, the processor 15 may be realized in various other forms of software and/or hardware. For purposes of description, only hardware components will be described hereinafter. However, it will be noted that the general inventive concept, and one or more embodiments thereof, will not be limited to those components shown in FIG. 1 or described in conjunction therewith.

Figure 2:
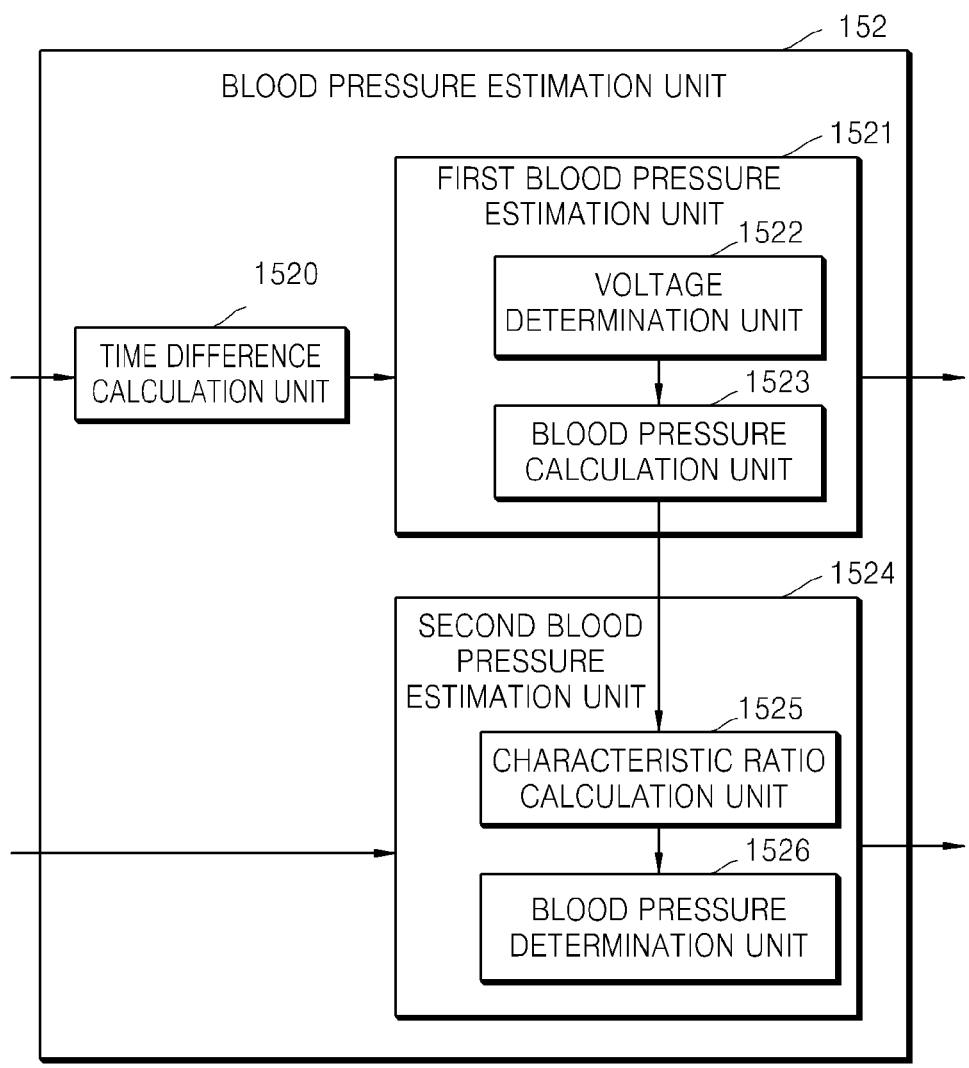
FIG. 2 is a block diagram illustrating a blood pressure estimation unit included in the blood pressure estimating apparatus illustrated in FIG. 1.

FIG. 2 is a block diagram illustrating the blood pressure estimation unit 152 included in the blood pressure estimating apparatus illustrated in FIG. 1. Referring to FIG. 2, the blood pressure estimation unit 152 includes a first blood pressure estimation unit 1521 and a second blood pressure estimation unit 1524. The first blood pressure estimation unit 1521 includes a voltage determination unit 1522 and a blood pressure calculation unit 1523, and the second blood pressure estimation unit 1524 includes a characteristic ratio calculation unit 1525 and a blood pressure determination unit 1526. The first blood pressure estimation unit 1521 estimates blood pressure in a blood pressure calculation mode, and the second blood pressure estimation unit 1524 estimates blood pressure in a characteristic ratio application mode, as will be described in further detail below.

In one or more embodiments, the blood pressure estimating apparatus 1 operates in one of at least two modes. Specifically, a first mode is the blood pressure calculation mode, and a second mode is the characteristic ratio application mode. More particularly, the blood pressure calculation mode is a mode in which the blood pressure of a user is estimated by calculating blood pressures in a body part of the user by sensing a sphygmus wave sensed when a vibration is applied to the body part of the user. On the other hand, the characteristic ratio application mode is a mode in which blood pressures of the body part of the user are determined using a blood pressure characteristic ratio of the user. Hereinafter, for clarification of description, the blood pressure estimation unit 152 will be described as operating in the blood pressure calculation mode, unless it is specifically noted that the characteristic ratio application mode is being described.

Referring still to FIG. 1, the blood pressure estimating apparatus 1 according to one or more embodiments includes all instruments and apparatuses for measuring blood pressure, such as a blood pressure instrument, a blood pressure meter and/or a hemadynamometer, for example.

The term "blood pressure" refers to a pressure exerted on the walls of blood vessels by blood that is pumped out of the heart and flows through the blood vessels. In addition, blood pressure may be classified as arterial blood pressure, capillary blood pressure or venous blood pressure, for example, depending on a type of the blood vessel in which the blood pressure is measured. In addition, blood pressure includes systolic blood pressure, when blood flows into the arteries as the ventricles of the heart contract, and diastolic blood pressure, when pressure is exerted on the arterial walls due to elasticity of the arterial walls when the ventricles expand and blood stays in the ventricles.

A sphygmus wave is a wave generated as a pulse (e.g., a sphygmus) is transmitted to peripheral arterioles. Thus, the term "sphygmus" indicates that an artery repetitively expands and relaxes, e.g., contracts, due to the flow of blood through the artery when the heart beats. Specifically, when the heart contracts, blood is supplied to the entire body from the heart through a main artery, such as the aorta, and thus pressure in the aorta varies. Such a change of the pressure in the main artery is transferred to the peripheral arterioles of the hands and feet, for example, and a sphygmus wave shows the change of the pressure in a waveform corresponding to the sphygmus wave.

In general, blood pressure may be measured using a direct or an indirect method, an invasive or a noninvasive method and an intrusive or a nonintrusive method, for example. In the indirect method, pressure is measured when the bloodstream in a brachial artery or a radial artery is occluded, such as by winding a blood-pressure cuff around an area to be measured, and then applying pressure to the area by injecting air, for example, into the blood-pressure cuff Thus, the noninvasive method measures blood pressure from outside, e.g., without invading, the blood vessels. Likewise, the intrusive method uses a blood-pressure cuff to measure blood pressure, while the nonintrusive method measures blood pressure without using a blood-pressure cuff.

Examples of the noninvasive method include an auscultatory method, an oscillometric method, a method using a tonometer and a method using a pulse transit time ("PTT").

The oscillometric method and the method using a tonometer are used with a digitized apparatus for measuring blood pressure. More specifically, the oscillometric method estimates the systolic pressure and the diastolic pressure by detecting a pulse wave generated in a depressurization process that depressurizes a body part at a constant speed. Detection of the pulse wave is conducted after sufficiently pressurizing the body part, through which arterial blood flows, to block the arterial blood flow therethrough. This is similar to the Korotkoff sounds method. The oscillometric method may also be conducted using a pressurization process that pressurizes the body part at a constant speed. A pressure at which the amplitude of a pulse waveform is at a systolic or a diastolic level may be estimated as a function of the systolic pressure or the diastolic pressure, as compared to a pressure at which the amplitude of the pulse waveform is at a maximum. The systolic or diastolic level denotes a systolic or diastolic characteristic ratio, respectively. Alternatively, a pressure at which the amplitude of the pulse waveform varies greatly may be estimated as a function of the systolic pressure or the diastolic pressure. During the depressurization process of the body part at a constant speed after the pressurization process, the systolic pressure is estimated just before a point in time at which the amplitude of the pulse waveform is at a maximum, and the diastolic pressure is estimated just after a point in time at which the amplitude of the pulse waveform is at the maximum. In contrast, in pressurizing the body part at a constant speed, the systolic pressure is estimated just after the point in time at which the amplitude of the pulse waveform is at the maximum, and the diastolic pressure is estimated just before the point in time at which the amplitude of the pulse waveform is at the maximum.

The statistical systolic and diastolic characteristic ratios are obtained by statistically analyzing sphygmus waves obtained by pressurizing body parts of subjects who are randomly selected. In other words, the sizes of points where the amplitudes of the sphygmus waves of the people are maximum are normalized to be 1, and a mean value of systolic pressures of the people is calculated when the size of the point is 1, thereby obtaining a systolic characteristic ratio. Likewise, the mean value of diastolic pressures of the people is calculated when the size of the point is 1, thereby obtaining a diastolic characteristic ratio. By using the statistical characteristic ratios, systolic pressure and diastolic pressure may be measured using an instant pressure when the amplitude of the sphygmus wave has the maximum value. However, if the statistical characteristic ratio has an error, blood pressure may not be continuously and accurately measured.

Types of apparatuses for measuring blood pressure include, for example, a wrist-type hemadynamometer and a finger-type hemadynamometer, depending on the particular body part to be measured. In one or more embodiments, the blood pressure estimating apparatus 1 is a wrist-type hemadynamometer, using a user's wrist as an area to be measured, but it will be noted that, in additional embodiments, the blood pressure estimating apparatus 1 may be another type of hemadynamometer, such as a finger-type hemadynamometer, for example.

In one or more embodiments, the pressurizing unit 11 pressurizes the wrist of a user to sense a sphygmus wave of the user. The pressurizing unit 11 generates a pressure according to a signal received from the actuator 12. In other words, when the actuator 12 transmits a signal having a constant magnitude, or a signal having a vibrating wave, the pressurizing unit 11 generates a pressure in response to the transmitted signal. Hereinafter, a constant pressure and a vibrating pressure means a pressure generated according to the signal having the constant magnitude or the signal having the vibrating wave, respectively. The signal having the vibrating wave denotes a signal whose wave vibrates at a constant frequency. This constant frequency is generally a high frequency.

If the user selects the characteristic ratio application mode, the pressurizing unit 11 pressurizes the wrist of the user with a continuous pressure that continuously increases or, alternatively, pressurizes the wrist of the user with a discrete pressure that increases in a stepwise form.

Examples of the pressurizing method includes an entire pressurizing method using a blood pressure cuff, or a regional pressurizing method of applying pressure to a portion of the blood vessel. For example, the pressurizing unit 11 may pressurize the entire wrist area or, alternatively, a portion of the wrist area through which the radial artery passes.

The actuator 12 adjusts the pressure applied to the user's wrist with the pressurizing unit 11. Specifically, the actuator 12 transmits signals having different constant magnitudes, signals having different magnitudes and having fluctuating waveforms, or a signal having continuously increasing or decreasing magnitude, to the pressurizing unit 11. The pressurizing unit 11 pressurizes the wrist of the user with a pressure generated according to the signal received from the actuator 12. The vibration signal denotes a signal whose wave vibrates at a constant frequency, which generally is a high frequency. When the actuator 12 transmits the vibration signal, the frequency is maintained at a constant value while the sensing unit 14 senses the sphygmus wave.

If the user selects the characteristic ratio application mode, the actuator 12 transmits a continuous signal or, alternatively, a discrete signal to the pressurizing unit 11. The continuous signal continuously increases, while the discrete signal increases in a stepwise form, e.g., increases in discrete steps, each having larger magnitudes relative to the immediately adjacent preceding step.

It will be noted that the blood pressure estimating apparatus 1 is not limited to only one pressurizing method and may be applied to all pressurizing methods. In addition, it will be noted that the user may easily change the frequency according to usage environments.

The vibration application unit 13 applies a vibration to a body part, e.g., the wrist, of the user. The vibration signal is a signal having a wave that vibrates at a constant frequency, which may be a high frequency. The frequency is set to be maintained constant while the sensing unit 14 senses the sphygmus wave. The vibration application unit 13 according to one or more embodiments uses an exciter. Types of the exciter include an eccentric motor, a piezoelectric film or a speaker, for example.

Figure 3A:
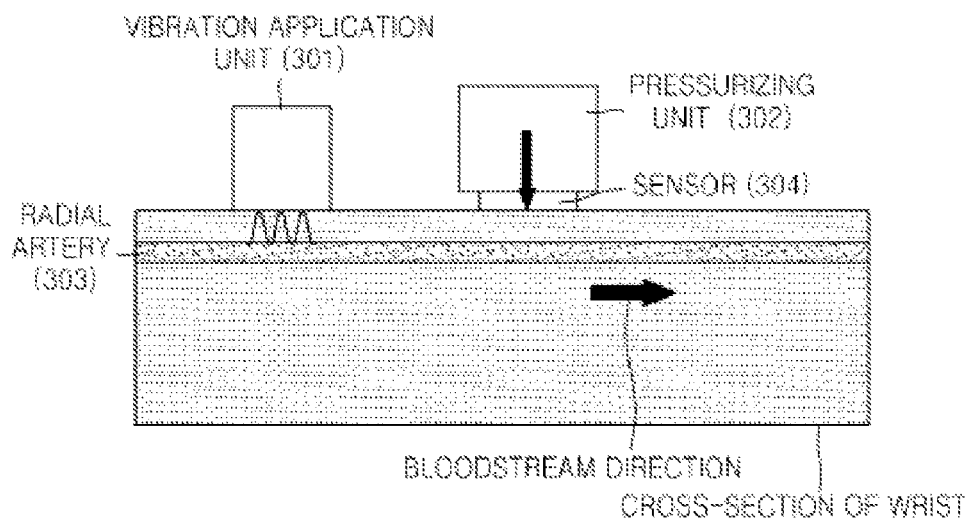
FIG. 3A is a partial cross-sectional view that illustrates application of a vibration to a wrist of a user by a vibration application unit and pressurization of the wrist of the user by a pressurizing unit according to an embodiment.

FIG. 3A is a partial cross-sectional view that illustrates application of a vibration to a wrist of a user by a vibration application unit and pressurization of the wrist of the user by a pressurizing unit according to an embodiment. More particularly, FIG. 3 illustrates application of a vibration to the wrist of a user by a vibration application unit 301 and pressurization of the wrist of the user by a pressurizing unit 302.

Referring to FIG. 3A, due to a bloodstream flow direction in a radial artery 303, the radial artery 303 first vibrates due to a vibration received from the vibration application unit 301, and is thereafter pressurized by the pressurizing unit 302.

More specifically, the vibration application unit 301 applies the vibration to the radial artery 303, and the pressurizing unit 302 pressurizes the vibration-applied radial artery 303 with different constant pressures. Thereafter, the vibration application unit 301 stops applying the vibration, whereas the pressurizing unit 302 continues pressurizing the radial artery 303. Accordingly, the radial artery 303 is first affected by both the vibration and the pressures, but thereafter the radial artery 303 is only affected by the pressures, since the vibration has been stopped. This change is reflected in the sphygmus wave of the radial artery 303, and a sensor 304 which contacts the skin of the user senses the corresponding sphygmus wave.

In one or more additional embodiments, the vibration application unit 301 applies a vibration to the radial artery 303, and the pressurizing unit 302 pressurizes the vibration-applied radial artery 303 with different constant pressures. Accordingly, the radial artery 303 is affected by both the applied vibration and the applied pressures. This is reflected in the sphygmus wave detected in the radial artery 303, and the sensor 304, which contacts the skin of the user senses, the corresponding sphygmus wave. Thus, in one or more embodiments, the sphygmus wave of the radial artery 303 that is affected by only a pressure, since the vibration application unit 301 stops applying the vibration, while the pressurizing unit 302 continues applying the pressure to the radial artery 303.

Figure 3B:
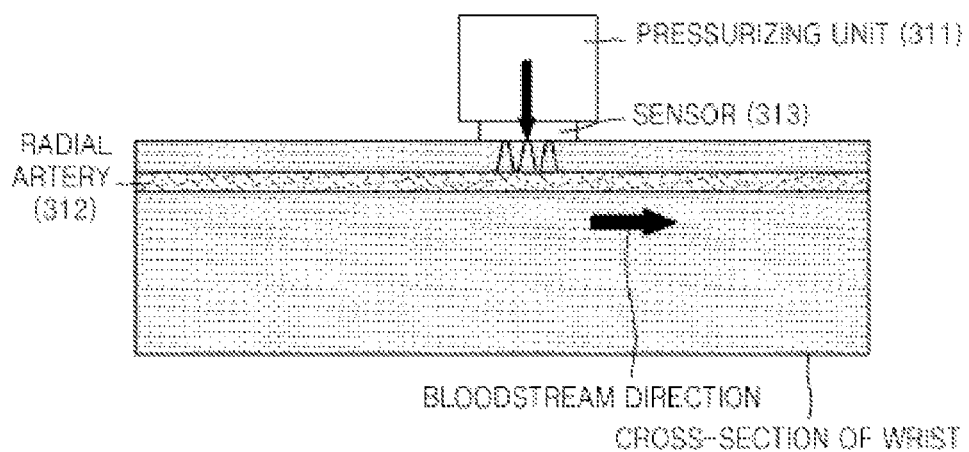
FIG. 3B is a partial cross-sectional view that illustrates pressurization of a wrist of a user by a pressurizing unit according to another embodiment.

FIG. 3B is a partial cross-sectional view that illustrates pressurization of a wrist of a user by a pressurizing unit 311 according to another embodiment. Referring to FIG. 3B, no vibration application unit 301 exists (in contrast with the embodiment shown in FIG. 3A), and a radial artery 312 is therefore pressurized only by the pressurizing unit 311. Although no vibration application unit 301 exists, since the pressurizing unit 311 pressurizes the radial artery 312 with different vibrating pressures, an effect where both a vibration and a pressure are applied to the radial artery 312 is generated.

Specifically, the pressurizing unit 311 pressurizes the radial artery 312 with vibrating pressures having different magnitudes, and then pressurizes the radial artery 312 with a constant pressure. Accordingly, the radial artery 312 is first affected by the vibrating pressures, and thereafter the radial artery 312 is only affected by a non-vibrating pressure, since the only pressurizing unit 311 pressurizes the radial artery 312 with the constant pressure. This change is reflected in the sphygmus wave of the radial artery 312, and a sensor 313 which contacts the skin of the user senses the corresponding sphygmus wave.

In additional embodiments, the pressurizing unit 311 pressurizes the radial artery 312 with different vibrating pressures. Accordingly, the radial artery 312 is affected by only a pressure component, which is reflected in the sphygmus wave of the radial artery 312, and the sensor 313 which contacts the skin of the user senses the corresponding sphygmus wave.

Referring again to FIG. 1, the control unit 153 controls the pressurization of the wrist of the user and the application of the vibration to the wrist of the user. Thus, the control unit 153 controls the actuator 12 and the vibration application unit 13 to determine what pressure is to be applied to the wrist of the user, as well as what frequency of vibration is to be applied to the wrist of the user. The control unit 153 also controls either only a pressure to be applied to the wrist of the user, or both the pressure and the vibration to be applied to the wrist of the user.

More specifically, according to one or more embodiments, the control unit 153 controls the vibration application unit 13 to apply a vibration to the wrist of the user and the pressurizing unit 11 to pressurize the wrist of the user with different constant pressures. Thereafter, the control unit 153 controls the pressurizing unit 11 to pressurize the wrist of the user with a constant pressure. In additional embodiments, the control unit 153 controls the vibration application unit 13 to apply a vibration to the wrist of the user, and the pressurizing unit 11 to pressurize the wrist of the user with different constant pressures.

According to yet another additional embodiment, the control unit 153 controls the pressurizing unit 11 to pressurize the wrist of the user with different vibrating pressures, and also controls the pressurizing unit 11 to pressurize the wrist of the user with a constant pressure. According to still another embodiment, the control unit 153 controls the pressurizing unit 11 to pressurize the wrist of the user with different vibrating pressures.

The control unit 153 controls the actuator 12 to determine a magnitude and/or a frequency of a signal transmitted to the pressurizing unit 11, to determine a value of a pressure applied to the body part of the user, which is to be measured, is to be pressurized by the pressurizing unit 11, and also controls the vibration application unit 13 to determine a frequency of vibration that is to be applied to the body part of the user.

Referring back to FIGS. 3A and 3B, the control unit 153 controls the vibration application unit 301 and an actuator to control vibration and pressure to be applied to the body part. Alternatively, the control unit 153 controls only the actuator to control pressure to be applied to the body part.

The sensing unit 14 senses a sphygmus wave of the body part of the user, which is to be measured, when a vibration has been applied to the body part of the user. The body part of the user corresponds to a part of the body from which blood pressure may be measured, such as the wrist, for example. The applied vibration denotes a vibration applied by the vibration application unit 13 or a vibrating pressure applied by the pressurizing unit 11. The sphygmus wave sensed by the sensing unit 14 includes a dynamic pressure component and a static pressure component. The sphygmus wave sensed by the sensing unit 14 is a sphygmus wave in which an influence of the applied vibration is reflected. In other words, the sensed sphygmus wave includes high-frequency vibration components.

The sensing unit 14 converts the sensed sphygmus wave into an electrical signal and transmits the electrical signal to the filtering unit 151 and the blood pressure estimation unit 152. When the user selects the characteristic ratio application mode, the sensing unit 14 transmits the sensed the sphygmus wave to the filtering unit 151. The electrical signal may be a current or a voltage, and hereinafter, the sphygmus wave will be described as being converted into a voltage, but it will be noted that the general inventive concept is not limited thereto. The sensing unit 14 senses the sphygmus wave in the wrist by using at least one sensor. In one or more embodiments, the sensor may be a pressure sensor, such as a piezoresistive pressure sensor or a capacitive pressure sensor, but the sensor may be any apparatus which senses a sphygmus wave, a value of which corresponds to a change of pressure in the wrist, and for converting the value into an electric signal.

Hereinafter, conversion of the sensed sphygmus wave into a voltage (e.g., a signal), will be described in further detail. In a radial artery of a user, the blood pressure transfers pressure around the radial artery and thereby acts as a pressure source. A change of the transferred pressure corresponds to a sphygmus wave sensed by the sensing unit 14. A pressure on a local surface, which may be directly on the radial artery, has a substantially linear relationship to an actual blood pressure in the radial artery, because the actual blood pressure, while somewhat decreased, is reflected in the local surface without substantial or non-linear changes. Thus, when the pressure on the local surface is determined, the actual blood pressure may be estimated using the linear relationship between the pressure on the local surface and the actual blood pressure in the radial artery. Put another way, since a change of the sphygmus wave sensed by the sensing unit 14 denotes a change of the pressure on the local surface due to the actual blood pressure in the radial artery, the blood pressure in the user's wrist which is to be measured may be estimated based on the sensed sphygmus wave. Specifically, in one or more embodiments, the linear relationship between local (sensed) and actual blood pressure is defined by in Equation 1, below.

$$P_S = m \cdot BP + n \quad \text{Equation 1:}$$

In Equation 1, $P_S$ denotes pressure on a local surface of the user's wrist and corresponds to a pressure value of the sphygmus wave sensed by the sensing unit 14, BP denotes blood pressure estimated to be the actual blood pressure in the radial artery, and m and n are coefficients satisfying a linear relationship between $P_S$ and BP. Since m and n change according to the conditions of pressurizing the radial artery in the wrist, the blood pressure may be estimated when m and n are determined.

The estimated blood pressure BP is linearly related to the pressure $P_S$, and the pressure $P_S$ is linearly related to the voltage into which the pressure value of the sphygmus wave sensed by the sensing unit 14 has been converted. Thus, the linear relationship between the pressure Ps and the voltage may be represented by Equation 2, below.

$$V = a \cdot P_S + b \quad \text{Equation 2:}$$

In Equation 2, V denotes the voltage obtained by the sensing unit 14, $P_S$ denotes pressure on a local surface as described above, a denotes sensitivity of a pressure sensor, and b denotes a zero input bias of the pressure sensor. Here, a and b are constants for the pressure sensor to transmit a uniform voltage with respect to a uniform pressure, and a and b are preset during a calibration process of the pressure sensor.

By rearranging Equation 1 and Equation 2 into a single equation, a relationship between the estimated blood pressure BP and the voltage into which the value of the sensed sphygmus wave has been converted by the sensing unit 14 may be ascertained, as represented in Equation 3, below.

$$V = a \cdot m \cdot BP + a \cdot n + b \quad \text{Equation 3:}$$

Equation 3, which defines the relationship between the voltage V and the estimated blood pressure BP, may be rearranged as shown Equation 4, below.

$$BP = \alpha \cdot V + \beta \quad \text{Equation 4:}$$

In Equation 4, the coefficients of Equation 3 are rearranged to more simply represent the relationship between the voltage V and the estimated blood pressure BP. In Equation 4, $\alpha$ and $\beta$ are coefficients that are defined based on the coefficients used in Equations 1 through 3. In the coefficients used in Equations 1 through 3, a and b are fixed values, but m and n change according to pressure applied to the wrist, and thus $\alpha$ and $\beta$ also change according to the applied pressure. Referring to Equation 4, the estimated blood pressure BP may be ascertained when $\alpha$, $\beta$, and the voltage V are known. In other words, if blood pressures at two different points of time may be ascertained from the sensed sphygmus wave, blood pressures at the other points in time including a systolic blood pressure and a diastolic blood pressure may be ascertained.

As shown in Equations 1 through 4, above, the sensing unit 14 converts a change of the sensed sphygmus wave into a change of a voltage, e.g., into a converted voltage change. The sensing unit 14 transmits the converted voltage change to the filtering unit 151, the blood pressure estimation unit 152, or both. In other words, in one or more embodiments, a waveform of the sensed sphygmus wave is converted into a waveform of the voltage. Although the sphygmus wave is illustrated as a waveform of the voltage according to time, the above-described embodiments are not limited thereto.

Figure 4A:
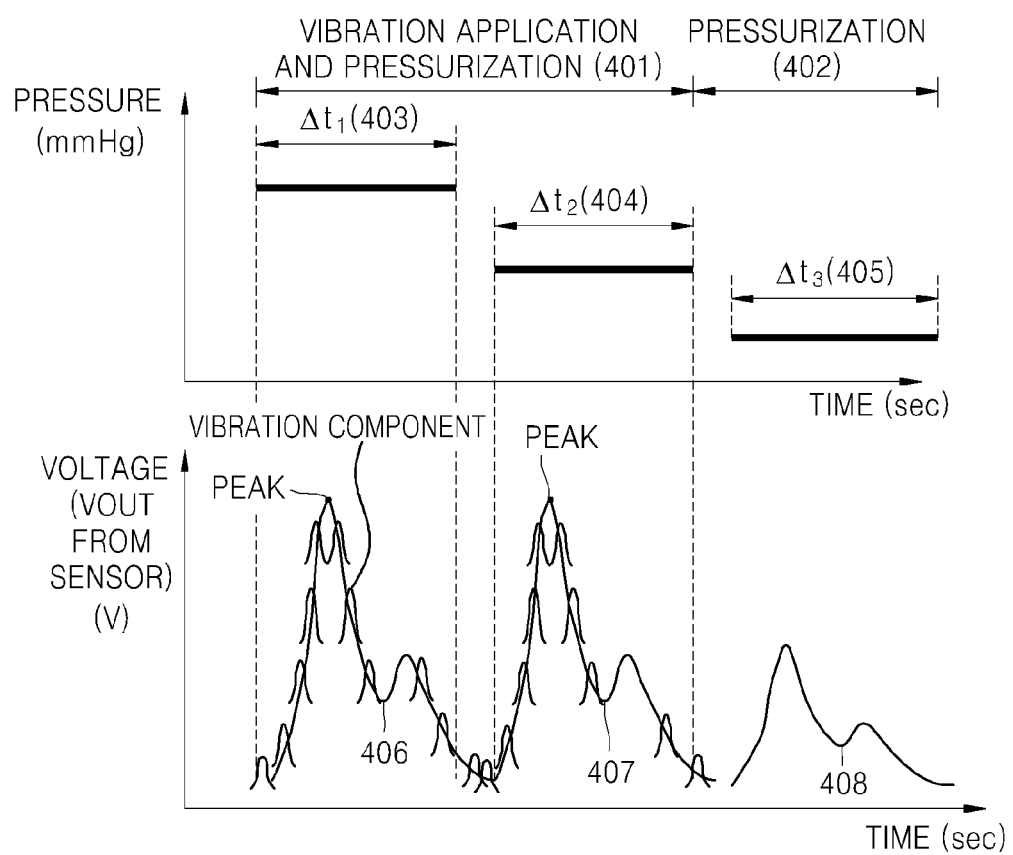
FIGS. 4A through 4D are graphs of pressure and voltage versus time showing sphygmus waves sensed by a sensing unit included in the blood pressure estimating apparatus illustrated in FIG. 1.
Figure 4B:
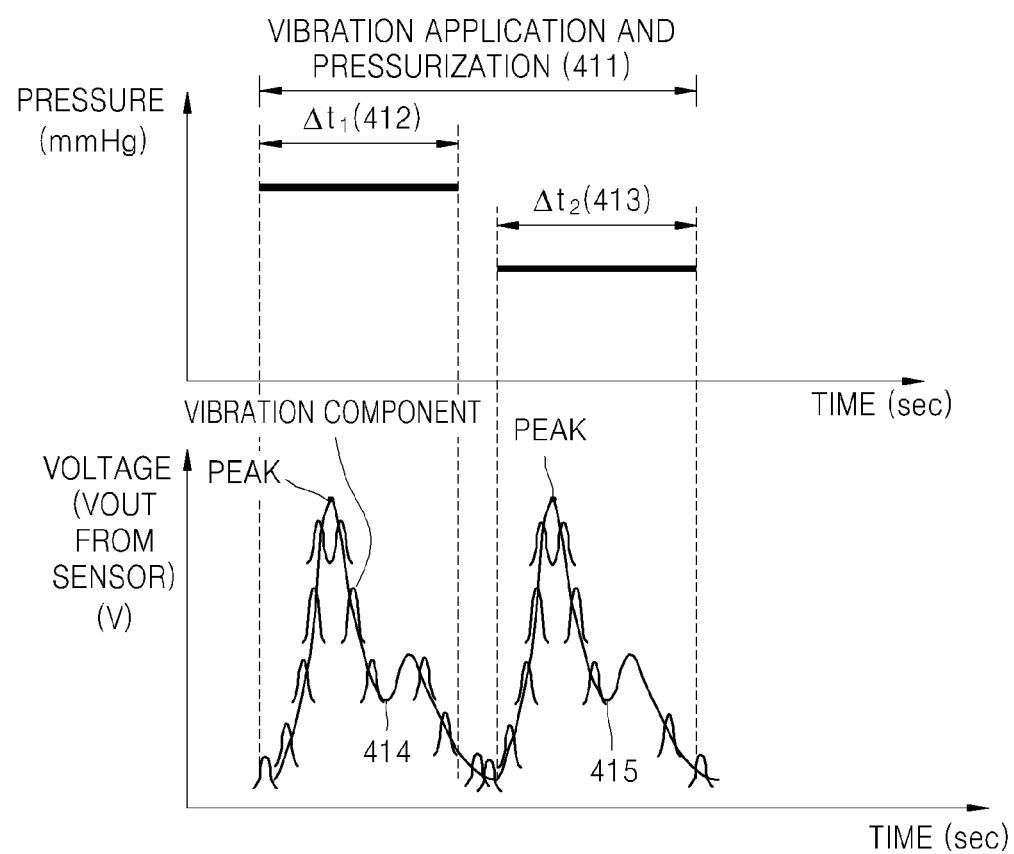
Figure 4C:
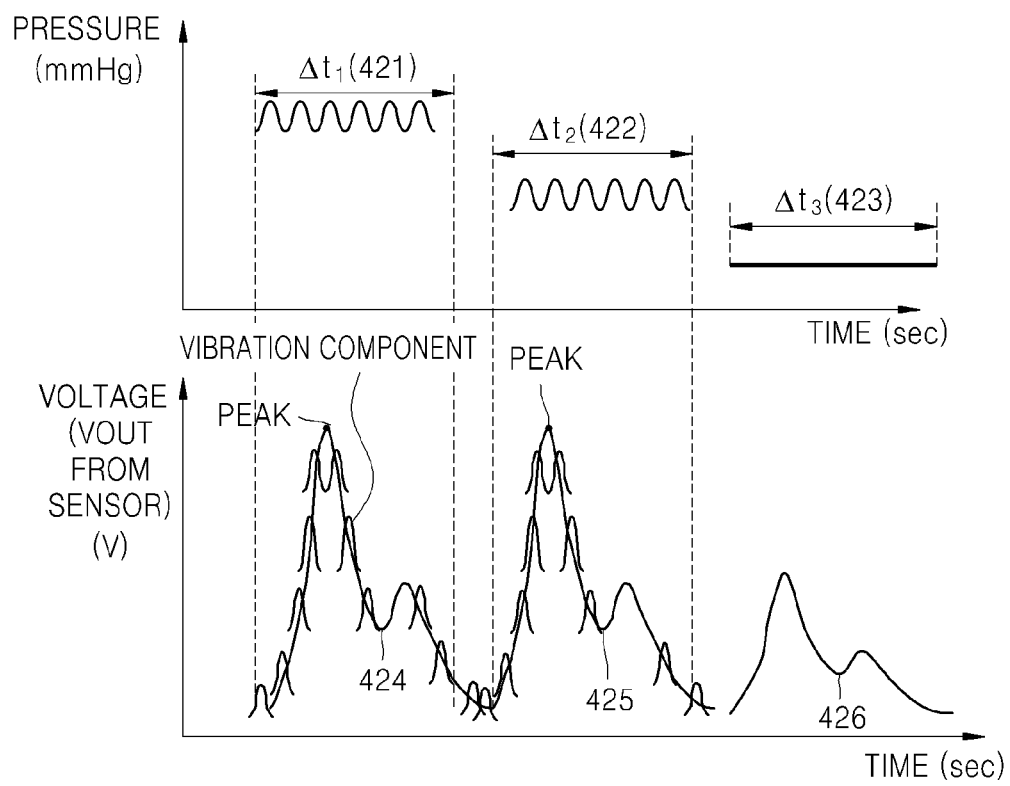
Figure 4D:
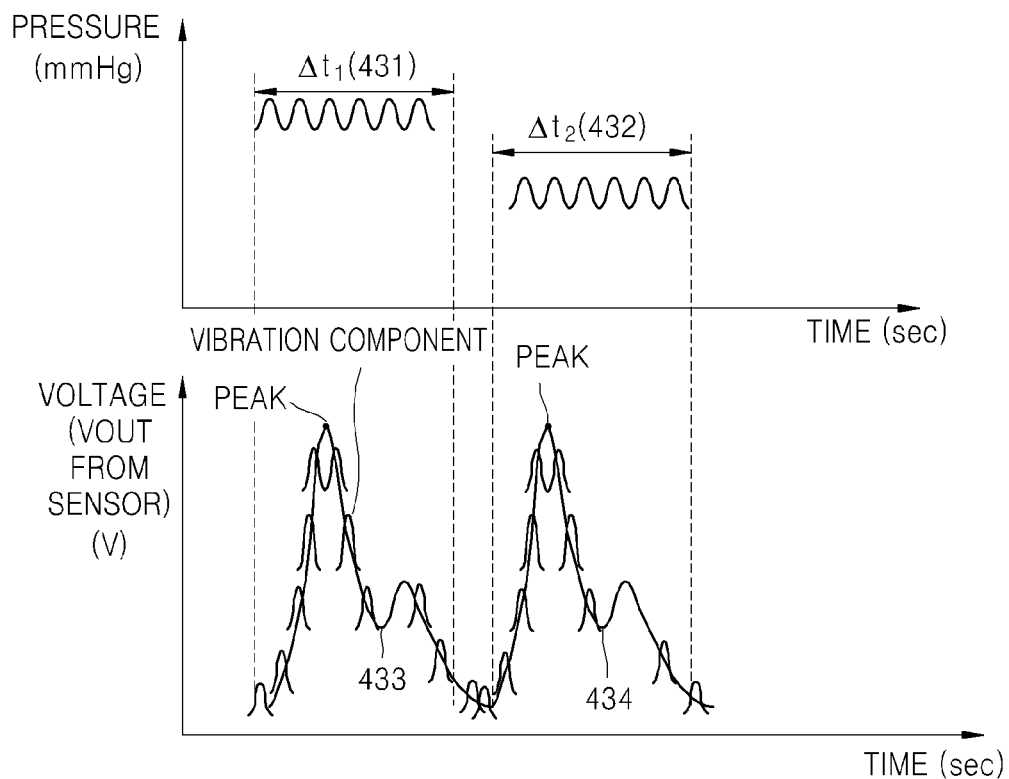

FIGS. 4A through 4D are graphs of pressure "P," in [units] and voltage "VOUT," in volts (V), versus time "t," in seconds, showing sphygmus waves sensed by one or more embodiments of a sensing unit, and method therefore, included in the blood pressure estimating apparatus 1 illustrated in FIG. 1. In the different embodiments shown in FIGS. 4A through 4D, the sensed sphygmus wave is illustrated as a waveform of a voltage according to time. Specifically, FIGS. 4A and 4B illustrate sphygmus waves affected by a vibration applied by the vibration application unit 13 and a pressure applied by the pressurizing unit 11, while FIGS. 4C and 4D illustrate sphygmus waves affected by vibrating pressures applied by the pressurizing unit 11. In each of FIGS. 4A through 4D, an upper graph shows a change of a signal transmitted from the actuator 12 according to time (t), and a lower graph shows a change of a voltage $V_{out}$ as a change of the sensed sphygmus wave according to the time (t). The pressure applied by the pressurizing unit 11 is generated according to the signal transmitted from the actuator 12.

Referring now to FIG. 4A, in operation 401, e.g., step 401 of one or more embodiments, the vibration application unit 13 applies a vibration to the wrist of a user and the pressurizing unit 11 pressurizes the wrist of the user. The vibration application unit 13 stops applying the vibration and the pressurizing unit 11 continues pressurizing the wrist of the user in operation 402. In other words, during times $\Delta t_1$ and $\Delta t_2$, the vibration application unit 13 and the pressurizing unit 11 apply vibrations to the wrist of the user and pressurize the wrist of the user with different constant pressures in operations 403 and 404, respectively. During a time $\Delta t_3$, in operation 405, the pressurizing unit 11 pressurizes the wrist of the user with a pressure having a constant value. A sphygmus wave 406 sensed during the time $\Delta t_1$ (operation 403), and a sphygmus wave 407 sensed during the time $\Delta t_2$ (operation 404), are sphygmus waves corresponding to the applied constant pressures, together with vibration components depending on the applied vibrations. However, a sphygmus wave 408 sensed during the time $\Delta t_3$, 405, is a sphygmus wave depending on the applied constant pressure, and does not include vibration components since no vibrations are applied to the wrist of the user.

Referring to FIG. 4B, the vibration application unit 13 applies a vibration to the wrist of a user and the pressurizing unit 11 pressurizes the wrist of the user in operation 411. In other words, during times $\Delta t_1$ and $\Delta t_2$ (operations 412 and 413, respectively), the vibration application unit 13 and the pressurizing unit 11 apply vibrations to the wrist of the user and pressurizes the wrist of the user with different constant pressures. A sphygmus wave 414, sensed during the time $\Delta t_1$, and a sphygmus wave 415, sensed during the time $\Delta t_2$, include both sphygmus waves corresponding to the applied constant pressures and vibration components depending on the applied vibrations.

Referring now to FIG. 4C, first, the pressurizing unit 11 pressurizes the wrist of the user with different vibrating pressures. Thereafter, the pressurizing unit 11 pressurizes the wrist of the user with a constant pressure. In other words, during times $\Delta t_1$ and $\Delta t_2$, the pressurizing unit 11 pressurizes the wrist of the user with different vibrating pressures. Then, during a time $\Delta t_3$, during step 423, the pressurizing unit 11 pressurizes the wrist of the user with a constant pressure. A sphygmus wave 424, sensed during the time $\Delta t_1$, and a sphygmus wave 425, sensed during the time $\Delta t_2$, include both sphygmus waves corresponding to the applied vibrating pressures and vibration components corresponding to the applied vibrating pressures. However, a sphygmus wave 426, sensed during the time $\Delta t_3$, includes only a sphygmus wave corresponding to the applied constant pressure.

Referring now to FIG. 4D, the pressurizing unit 11 pressurizes the wrist of the user with different vibrating pressures. In other words, during times $\Delta t_1$ and $\Delta t_2$, the pressurizing unit 11 pressurizes the wrist of the user with different vibrating pressures. A sphygmus wave 433 sensed during the time $\Delta t_1$, and a sphygmus wave 434 sensed during the time $\Delta t_2$, include both sphygmus waves corresponding to the applied vibrating pressures and vibration components corresponding to the applied vibrating pressures.

Figure 5:
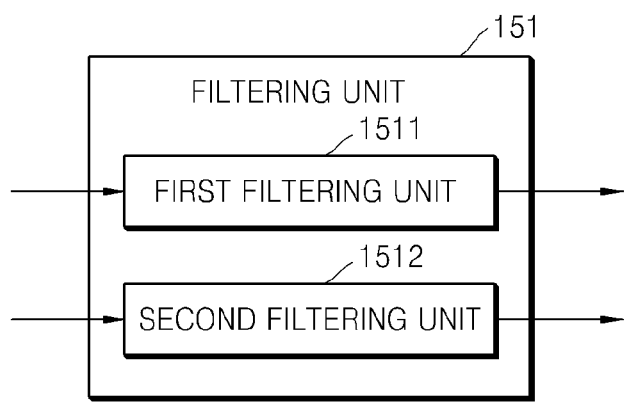
FIG. 5 is a block diagram illustrating a filtering unit included in the blood pressure estimating apparatus illustrated in FIG. 1.

FIG. 5 is a block diagram illustrating an embodiment of the filtering unit 151 illustrated in FIG. 1. Referring to FIG. 5, the filtering unit 151 includes a first filtering unit 1511 and a second filtering unit 1512.

In one or more embodiments, the first filtering unit 1511 performs filtering by extracting, e.g., filtering out, a high-frequency signal, having a frequency in a frequency band of the applied vibration, from the sphygmus wave sensed by the sensing unit 14. Thus, the first filtering unit 1511 in an embodiment is a high pass filter ("HPF"). A cutoff frequency of the HPF is set to be a frequency between a frequency of the sensed sphygmus wave and a frequency of the applied vibration. Since the radial artery is affected by a vibration applied by the vibration application unit 13 or the pressurizing unit 11, the sphygmus wave sensed by the sensing unit 14 includes a high-frequency vibration component. The filtered-out high-frequency signal denotes the high-frequency vibration component. The first filtering unit 1511 transmits the extracted, e.g., filtered out, high-frequency signal to a time difference calculation unit 1520 (FIG. 2).

The second filtering unit 1512 performs filtering by extracting, e.g., filtering out, a low-frequency signal having a frequency lower than the frequency of the applied vibration from the sphygmus wave sensed by the sensing unit 14. Here, the second filtering unit 1512 corresponds to a low pass filter ("LPF"). A cutoff frequency of the LPF is set to be a frequency lower than the frequency of the applied vibration. Since the sphygmus wave sensed by the sensing unit 14 includes a high-frequency vibration component as described above, the original sphygmus wave of the radial artery, from which the high-frequency vibration component has been removed, may be obtained by extracting the low-frequency signal having a cutoff frequency lower than the frequency of the applied vibration. Thus, the filtered-out low-frequency signal denotes the original sphygmus wave of the radial artery not affected by the vibration. The second filtering unit 1512 transmits the extracted, e.g., filtered-out, low-frequency signal to at least one of the group consisting of the time difference calculation unit 1520, the voltage determination unit 1521, and the blood pressure calculation unit 1522.

If the user selects the characteristic ratio application mode, the first and second filtering units 1511 and 1512, respectively, filter the sphygmus wave by extracting the filtered-out high-frequency signal and the filtered-out low-frequency signal, respectively, by using a cutoff frequency different from a cutoff frequency used in the blood pressure calculation mode. In the characteristic ratio application mode, the first filtering unit 1511 and the second filtering unit 1512 transmit the filtered-out high-frequency signal and the filtered-out low-frequency signal to the characteristic ratio calculation unit 1525 and the blood pressure determination unit 1526, respectively.

Figure 6:
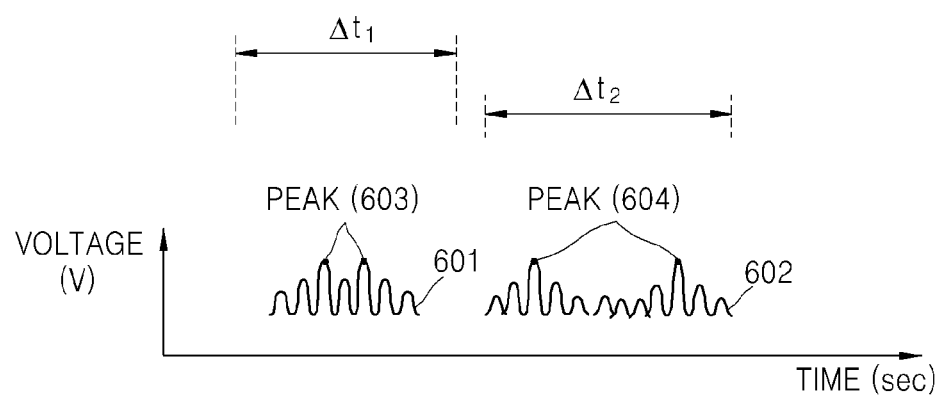
FIG. 6 is a graph of voltage versus time showing high-frequency signals extracted by a first filtering unit included in the filtering unit illustrated in FIG. 5.

FIG. 6 is a graph of voltage versus time showing high-frequency signals extracted, e.g., filtered-out, by the first filtering unit 1511 illustrated in FIG. 5, according to one or more embodiments. Referring to FIG. 6, a filtered-out high-frequency signal 601 extracted during a time $\Delta t_1$ and a filtered-out high-frequency signal 602 extracted during a time $\Delta t_2$ have waveforms of voltages varying according to time. The time $\Delta t_1$ represents the times corresponding to operations 403, 412, 421 and 431 of FIGS. 4A through 4D, and the time $\Delta t_2$ represent the times corresponding to operations 404, 413, 422 and 432 of FIGS. 4A through 4D. Each of the high-frequency signals 601 and 602 includes points of time that represent peaks thereof. The points of time are points of time when a transmural pressure is zero (0).

More specifically, blood is pushed to the arteries due to the contractions and expansions of the user's heart, and the blood pressure in the arteries repeatedly increases and decreases due to these repetitive actions of the heart. Accordingly, the arteries contract or expand according to a variation of the pressure in the arteries, and a sphygmus wave is generated according to the variation of the pressure. A pressure exerted on the wall of the blood vessel of a radial artery is referred to as a transmural pressure. If a radial artery which repeatedly contracts or expands is pressurized with a constant pressure, the radial artery is pressed with the applied pressure and occluded. Thus, the transmural pressure increases. However, over time, the radial artery which repeatedly contracts or expands periodically is balanced between an externally applied pressure and the blood pressure in the radial artery, and thus there exist points of time when the transmural pressure is 0. In other words, the points of time when the transmural pressure is 0 are points of time when the blood pressure of the radial artery is equal to the externally applied pressure.

The radial artery is pressurized with a constant pressure, and a vibration is applied to the radial artery. Alternatively, the radial artery is pressurized with a vibrating pressure. A point of time when the high-frequency signal 601 or 602, extracted by the first filtering unit 1511, peaks corresponds to a point of time when the transmural pressure is 0. Thus, a pressure applied at this point of time is equal to the blood of the radial artery.

Referring to FIG. 6, at points of time 603, when the high-frequency signal 601 extracted during the time $\Delta t_1$ peaks, and points of time 604, when the high-frequency signal 602 extracted during the time $\Delta t_2$ peaks, the transmural pressure is 0 and the applied pressure is equal to the blood of the radial artery.

Figure 7A:
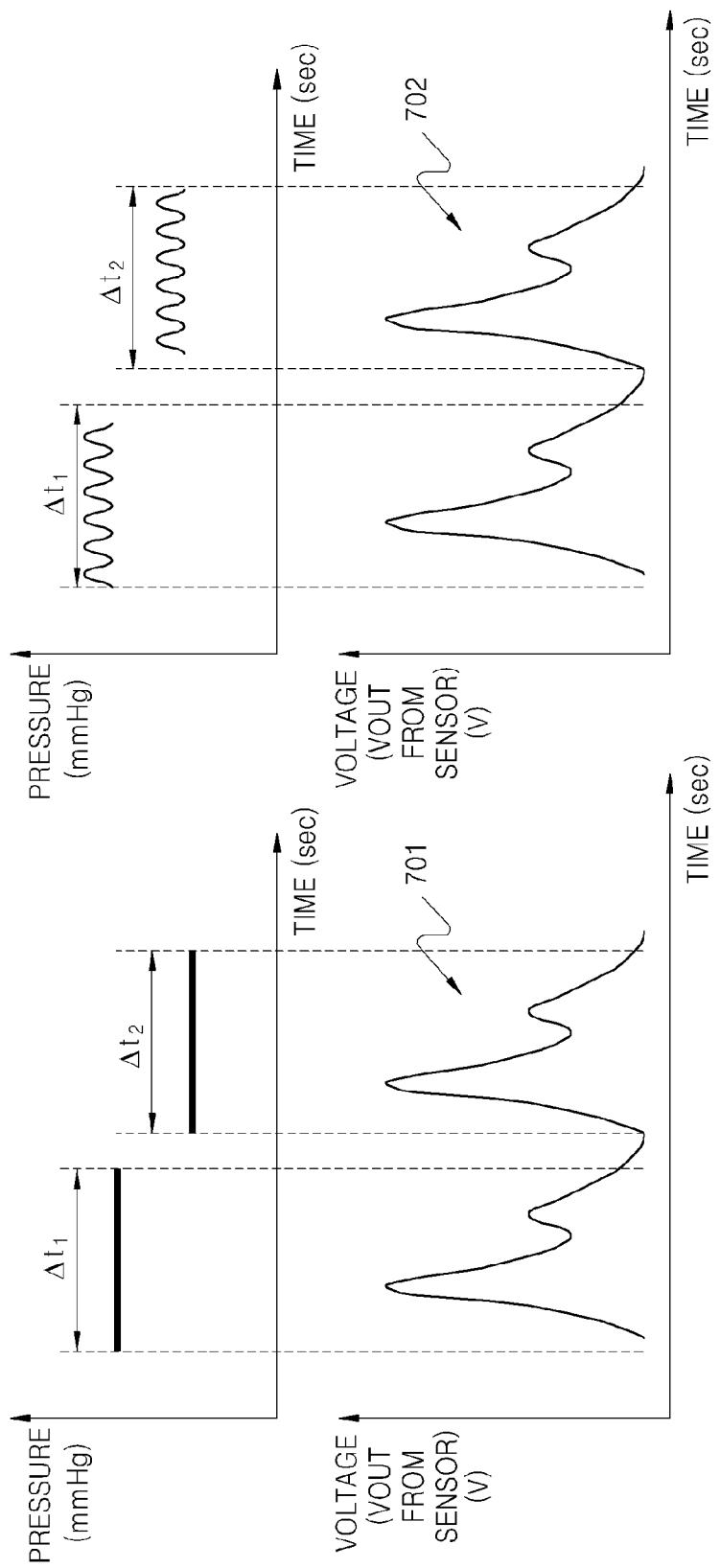
FIG. 7A includes graphs of voltage and pressure versus time showing a low-frequency signal extracted by a second filtering unit included in the filtering unit illustrated in FIG. 5.

FIG. 7A includes graphs of voltage and pressure versus time showing a low-frequency signal extracted by the second filtering unit 1512 included in the filtering unit 151 illustrated in FIG. 5. Referring to FIG. 7A, a filtered-out low-frequency signal 701 on the left side is a low-frequency signal extracted by the second filtering unit 1512 by using the sphygmus waves sensed during times $\Delta t_1$ and $\Delta t_2$ when the vibration application unit 13 applies a vibration and the pressurizing unit 11 applies different constant pressures, and a filtered-out low-frequency signal 702 on the right side is a low-frequency signal extracted by the second filtering unit 1512 by using the sphygmus waves sensed during times $\Delta t_1$ and $\Delta t_2$ when the pressurizing unit 11 applies different vibrating pressures.

Figure 7B:
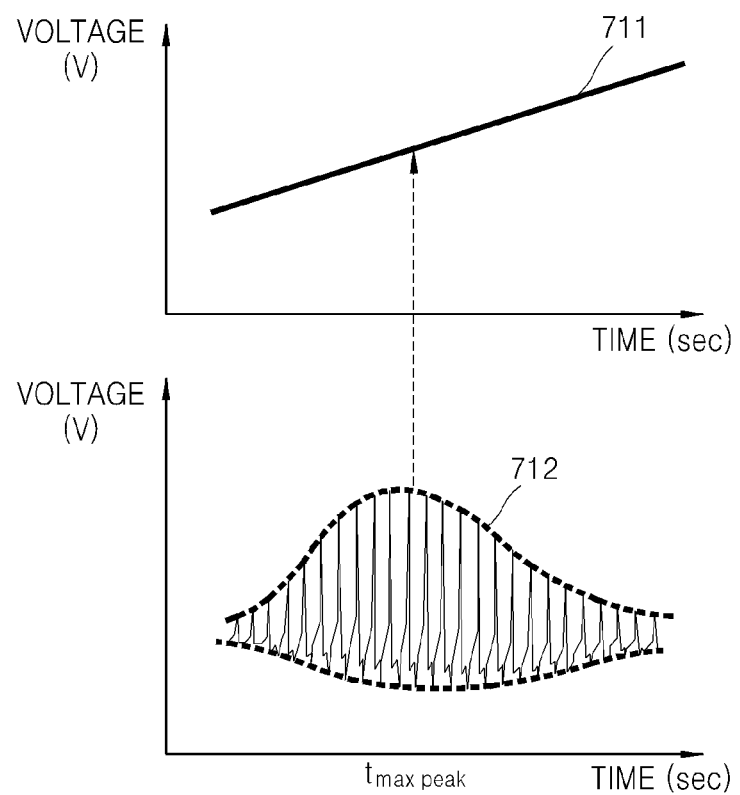
FIG. 7B includes graphs of voltage versus time showing a high-frequency signal and a low-frequency signal extracted by the first and second filtering units included in the filtering unit illustrated in FIG. 5.

FIG. 7B includes graphs of voltage versus time showing a high-frequency signal and a low-frequency signal extracted by the first and second filtering units 1511 and 1512, respectively, included in the filtering unit 151 illustrated in FIG. 5, in the characteristic ratio application mode according to an embodiment. If the user selects the characteristic ratio application mode, the pressurizing unit 11 pressurizes the wrist of the user with a continuous pressure, e.g., a pressure that continuously increases, or, alternatively, pressurizes the wrist of the user with a discrete pressure that increases in a stepwise form over time. The sensing unit 14 senses a sphygmus wave from the wrist of the user that is being pressurized as described above.

Referring to FIG. 7B, in the characteristic ratio application mode, the second filtering unit 1512 filters out a low-frequency signal 711 by passing the sphygmus wave sensed in the characteristic ratio application mode through the LPF. In the characteristic ratio application mode, the first filtering unit 1511 filters out a high-frequency signal 712 by passing the sphygmus wave sensed in the characteristic ratio application mode through the HPF. Thus, the low-frequency signal 711 and the low-frequency signal 712 is obtained in the characteristic ratio application mode using the blood pressure estimating apparatus 1 according to one or more embodiments.

Referring again to FIG. 2, the time difference calculation unit 1520 calculates time differences between points of time corresponding to peaks of the sensed sphygmus wave and points of time corresponding to the peaks of the filtered sphygmus wave. The points of time corresponding to the peaks of the filtered sphygmus wave are points of time corresponding to the peaks of the high-frequency signal extracted by the first filtering unit 1511. The points of time corresponding to the peaks of the extracted high-frequency signal are when the transmural pressure is 0, as described above.

When durations during which a vibration is applied and a constant pressure is applied are different from a duration when only a constant pressure is additionally applied, a time difference therebetween is normalized. If a duration when a vibrating pressure is applied is different from a duration when only a constant pressure is additionally applied, a time difference therebetween is normalized. The normalized time difference is transmitted to the voltage determination unit 1521.

Figure 8A:
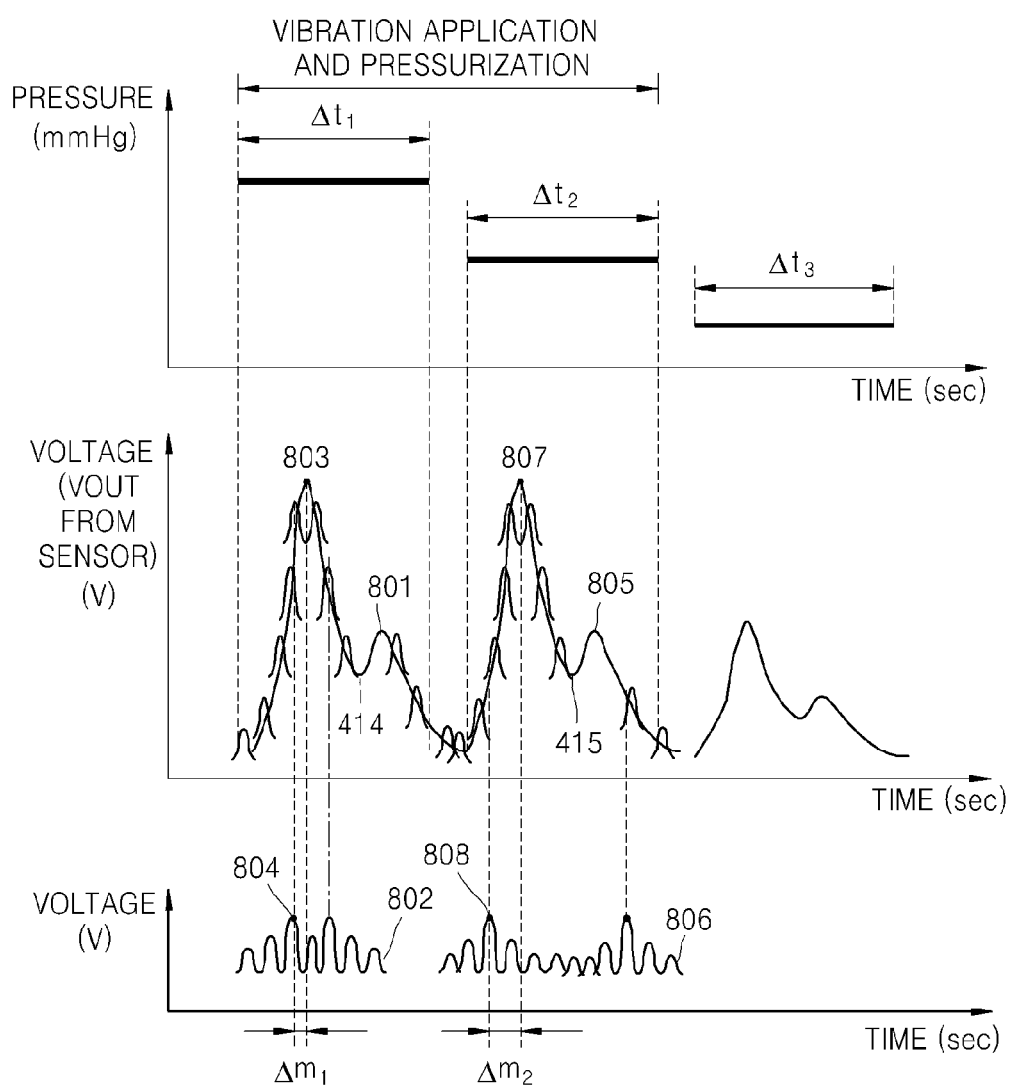
FIGS. 8A and 8B are graphs of voltage and pressure versus time showing calculations of time differences performed by a time difference calculation unit included in the blood pressure estimation unit illustrated in FIG. 2.
Figure 8B:
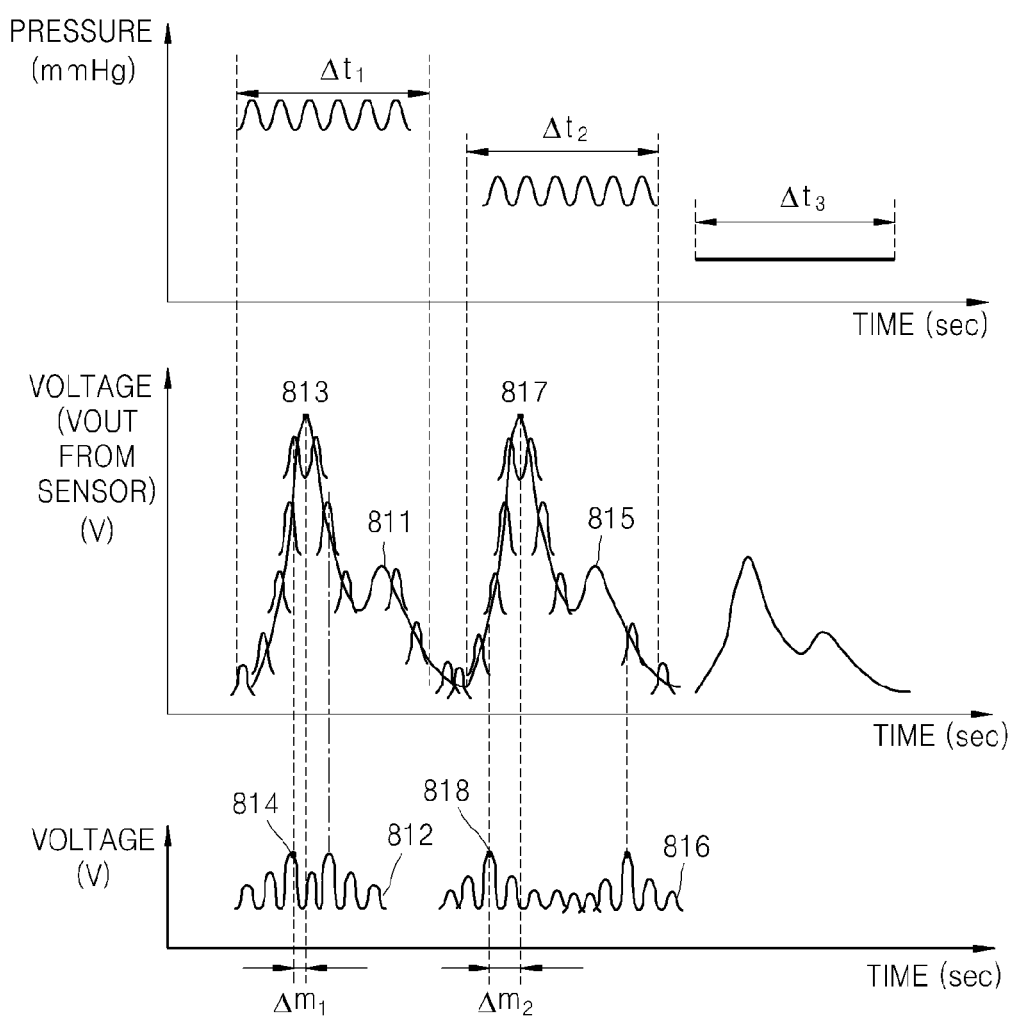

FIGS. 8A and 8B are graphs of voltage and pressure versus time showing calculations of time differences performed by the time difference calculation unit 1520 illustrated in FIG. 2.

Referring to FIG. 8A, during a time $\Delta t_1$, the vibration application unit 13 applies a vibration to the wrist of a user and the pressurizing unit 11 pressurizes the wrist of the user with a constant pressure. During a time $\Delta t_2$, the vibration application unit 13 applies a vibration to the wrist of the user and the pressurizing unit 11 pressurizes the wrist of the user with a constant pressure. A time difference $\Delta m_1$ between a point of time 803 representing a peak of a sphygmus wave 801 sensed by the sensing unit 14 during the time $\Delta t_1$ and a point of time 804 representing a peak of a high-frequency signal 802 extracted by the first filtering unit 1511 during the time $\Delta t_1$ is calculated. A time difference $\Delta m_2$ between a point of time 807 representing a peak of a sphygmus wave 805 sensed by the sensing unit 14 during the time $\Delta t_2$ and a point of time 808 representing a peak of a high-frequency signal 806 extracted by the first filtering unit 1511 during the time $\Delta t_2$ is calculated.

If associated periods of the sphygmus waves 801 and 805 sensed during the times $\Delta t_1$ and $\Delta t_2$ are not equal to a period of a sphygmus wave sensed during a time $\Delta t_3$, the time differences $\Delta m_1$ and $\Delta m_2$ can not be used as they are, e.g., without modification or adjustment, because when a period of a sphygmus wave has different values, time differences between points of time when the sphygmus wave has peaks and points of time when the transmural pressure is 0 are not identical to each other. Thus, the time difference calculation unit 1520 calculates a new time difference $\Delta m_x$ by using a ratio of a period of the sphygmus wave sensed during the time $\Delta t_3$ to a period of the sphygmus wave sensed during the time $\Delta t_1$, and a new time difference $\Delta m_y$ by using a ratio of the period of the sphygmus wave sensed during the time $\Delta t_3$ to a period of the sphygmus wave sensed during the time $\Delta t_2$. In one or more embodiments, the new time differences $\Delta m_x$ and $\Delta m_y$ are calculated using Equation 5, below.

$$\frac{\Delta m_1}{\Delta T_1} = \frac{\Delta m_x}{\Delta T_3}, \frac{\Delta m_2}{\Delta T_2} = \frac{\Delta m_y}{\Delta T_3} \qquad \text{Equation 5:}$$

In Equation 5, $\Delta T_1$, $\Delta T_2$ and $\Delta T_3$ denote respective periods of the sphygmus waves sensed during the times $\Delta t_1$, $\Delta t_2$ and $\Delta t_3$, while $\Delta m_1$ and $\Delta m_2$ denote the time differences between the point of time 803 representing a peak of the sensed sphygmus wave 801 and the point of time 804 representing a peak of the high-frequency signal 802 and a time difference between the point of time 807 representing a peak of the sensed sphygmus wave 805 and the point of time 808 representing a peak of the high-frequency signal 806, respectively. Thus, the upper equation in Equation 5 is for calculating the new time difference $\Delta m_x$ corresponding to the time difference $\Delta m_1$ in the sphygmus wave having the period $\Delta T_3$, and the lower equation in Equation 5 is to calculate the new time difference $\Delta m_y$ corresponding to the time difference $\Delta m_2$ in the sphygmus wave having the period $\Delta T_3$. In other words, $\Delta m_x$ and $\Delta m_y$ denote the new time differences calculated using the time differences $\Delta m_1$ and $\Delta m_2$ so as to correspond to the sphygmus wave having the period $\Delta T_3$.

In the filtered-out high-frequency signals 802 and 806 (FIG. 8A), points of time correspond to when two peaks appear. Although a peak of a high-frequency signal appearing prior to a peak of a sensed sphygmus wave is used, additional embodiments are not limited thereto. In other words, a peak of the high-frequency signal appearing temporally after the peak of the sensed sphygmus wave may be used.

Referring now to FIG. 8B, during a time $\Delta t_1$, the pressurizing unit 11 pressurizes the wrist of the user with a vibrating pressure. During a time $\Delta t_2$, the pressurizing unit 11 pressurizes the wrist of the user with a vibrating pressure that is different in magnitude from the vibrating pressure applied during the time $\Delta t_1$. A time difference $\Delta m1$ between a point of time 813, representing a peak of a sphygmus wave 811 sensed by the sensing unit 14 during the time $\Delta t_1$, and a point of time 812, representing a peak of a high-frequency signal 812 extracted by the first filtering unit 1511 during the time $\Delta t_1$, is calculated. A time difference $\Delta m_2$ between a point of time 817 representing a peak of a sphygmus wave 815 sensed by the sensing unit 14 during the time $\Delta t_2$, and a point of time 818 representing a peak of a high-frequency signal 816 extracted by the first filtering unit 1511 during the time $\Delta t_2$ are calculated. If respective periods of the sphygmus waves 811 and 815, sensed during the times $\Delta t_1$ and $\Delta t_2$, respectively, are not equal to a period of a sphygmus wave sensed during a time $\Delta t_3$, new time differences $\Delta m_x$ and $\Delta m_y$ are calculated using Equation 5, above.

Similar as described above and shown in FIG. 8A, in the filtered-out high-frequency signals 812 and 816 of FIG. 8B, points of time correspond to two peaks. Although a peak of a high-frequency signal appearing prior to a peak of a sensed sphygmus wave is used, additional embodiments are not limited thereto. In other words, a peak of the high-frequency signal appearing after the peak of the sensed sphygmus wave may be used.

Referring again to FIG. 2, the first blood pressure estimation unit 1521 includes the voltage determination unit 1522 and the blood pressure calculation unit 1523. The first blood pressure estimation unit 1521 estimates blood pressures of a user's body part, based on time differences between the points of time corresponding to peaks of the sensed sphygmus wave and the points of time corresponding to peaks of the filtered sphygmus wave. The peaks of the filtered sphygmus wave are points of time corresponding to peaks of the high-frequency signal filtered out by the first filtering unit 1511. The first blood pressure estimation unit 1521 transmits the estimated blood pressures to the user interface unit 17, and the user interface unit 17 outputs the estimated blood pressures to the user. According to one or more embodiments, a maximum blood pressure from among the blood pressures estimated by the first blood pressure estimation unit 1521 may be estimated as a systolic blood pressure, and a minimum blood pressure from among the estimated blood pressures may be estimated as a diastolic blood pressure. It will be understood that other blood pressures, such as a mean blood pressure, for example, may be easily estimated with the blood pressure estimating apparatus 1 according to one or more embodiments described herein.

According to one or more embodiments, the voltage determination unit 1522 determines voltages corresponding to a sphygmus wave sensed while the application of vibration is interrupted, by using the time differences described above. The interruption of the application of vibration denotes that the vibration application unit 13 stops applying vibration and only the pressurizing unit 11 applies a constant pressure. According to additional embodiments, the voltage determination unit 1522 determines voltages corresponding to a sphygmus wave sensed while the wrist of the user is being pressurized with a constant pressure, by using the same time differences. The pressurization of the wrist of the user with the constant pressure denotes that the pressurizing unit 11 pressurizes the wrist of the user with a vibrating pressure and then pressurizes the wrist of the user with the constant pressure. According to additional embodiments, the voltage determination unit 1522 determines voltages corresponding to an extracted, e.g., a filtered-out, low-frequency signal, by using the time differences. The filtered-out low-frequency signal denotes the low-frequency signal extracted by the second filtering unit 1512. The pressure determination unit 1522 transmits the determined voltages to the blood pressure calculation unit 1523.

More specifically, the voltage determination unit 1522 determines voltages by using either the sphygmus wave sensed by the sensing unit 14 or the low-frequency signal extracted by the second filtering unit 1512 and the time differences calculated by the time difference calculation unit 1520. The sphygmus wave sensed by the sensing unit 14 denotes a sphygmus wave sensed while no vibrations are applied and only a constant pressure is applied. In other words, the sphygmus wave sensed by the sensing unit 14 denotes the sphygmus wave sensed during the time $\Delta t_3$ in FIGS. 8A and 8B.

The voltage determination unit 1521 determines voltages at points of time that differ from points of time when the sensed sphygmus wave, or the extracted low-frequency signal, peaks, by the time differences calculated in the time difference calculation unit 1520. When the time differences are normalized, a time representing the sensed sphygmus wave or the extracted low-frequency signal is normalized, and the voltage determination unit 1522 determines voltages of points of time that differ from points of time representing peaks of the sensed sphygmus wave or the extracted low-frequency signal, by the normalized time differences. Since the voltages determined by the voltage determination unit 1522 are the voltages of points of time corresponding to points of time when the high-frequency signal extracted by the first filtering unit 1511 peaks, the determined voltages may be considered as voltages of points of time when a transmural pressure is 0. Accordingly, pressures corresponding to the determined voltages are the same as actual blood pressures of the radial arteries.

Figure 9A:
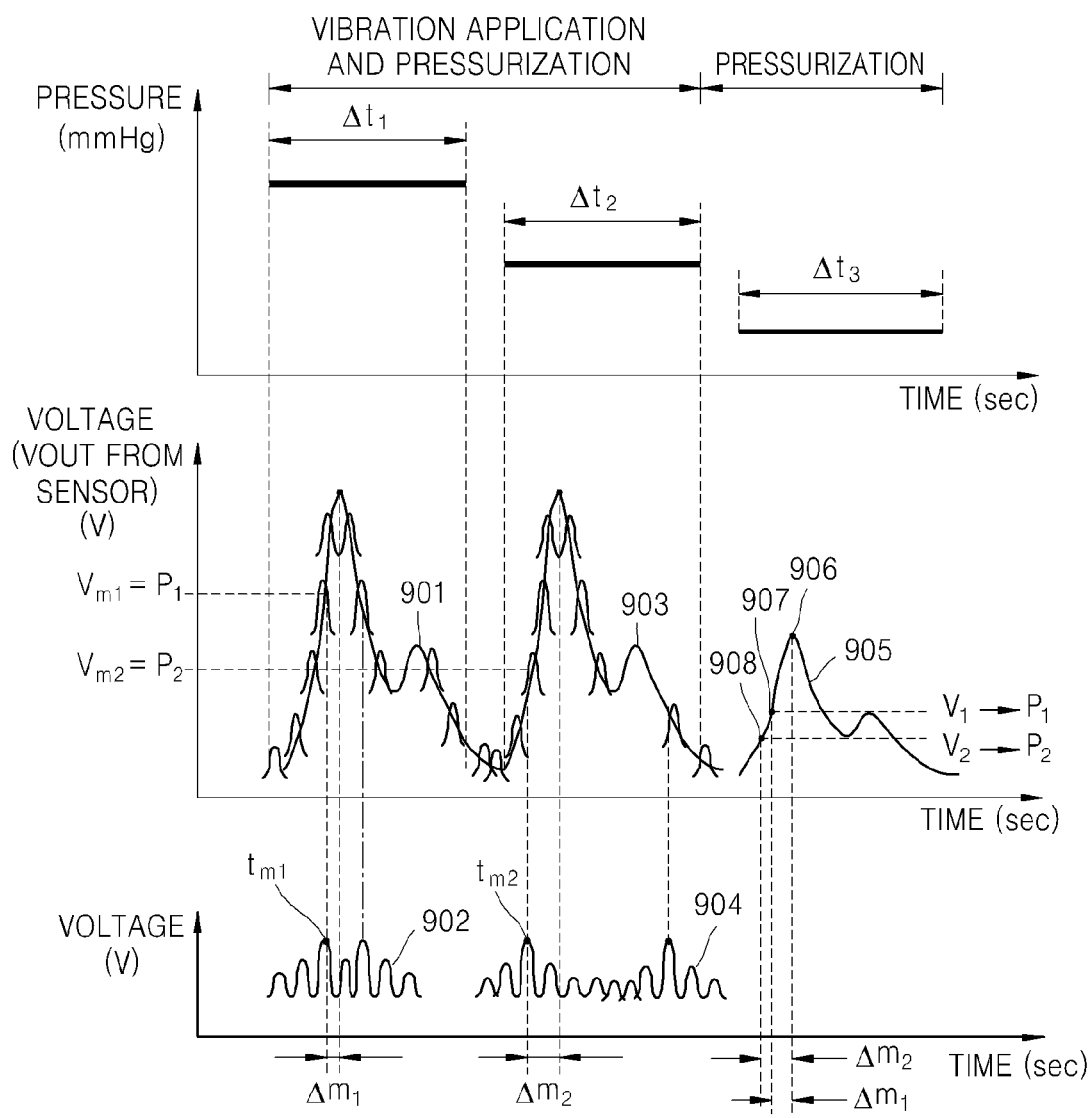
FIGS. 9A through 9D are graphs of voltage and pressure versus time showing determinations of voltages by a voltage determination unit included in the blood pressure estimation unit illustrated in FIG. 2.
Figure 9B:
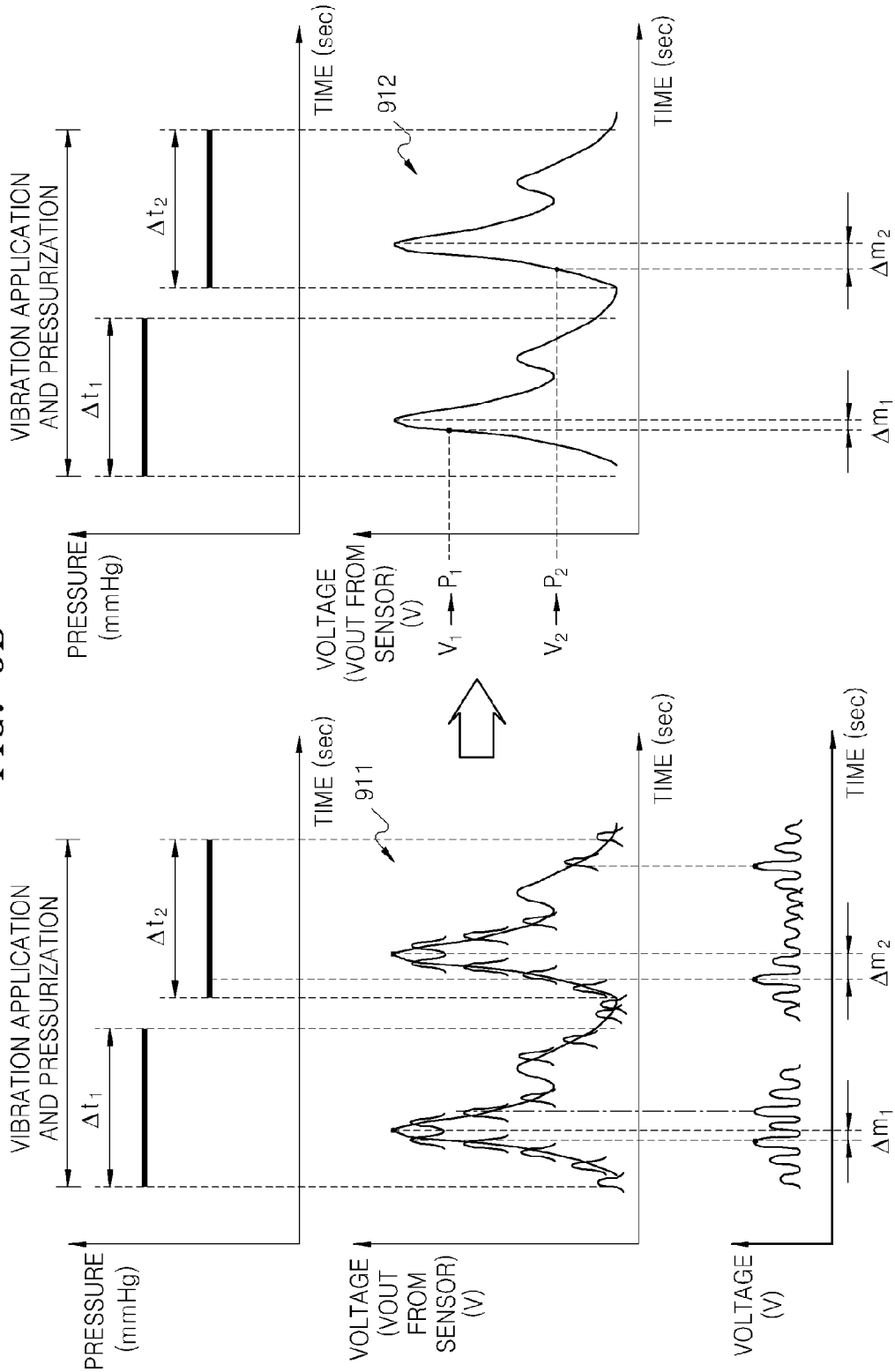
Figure 9C:
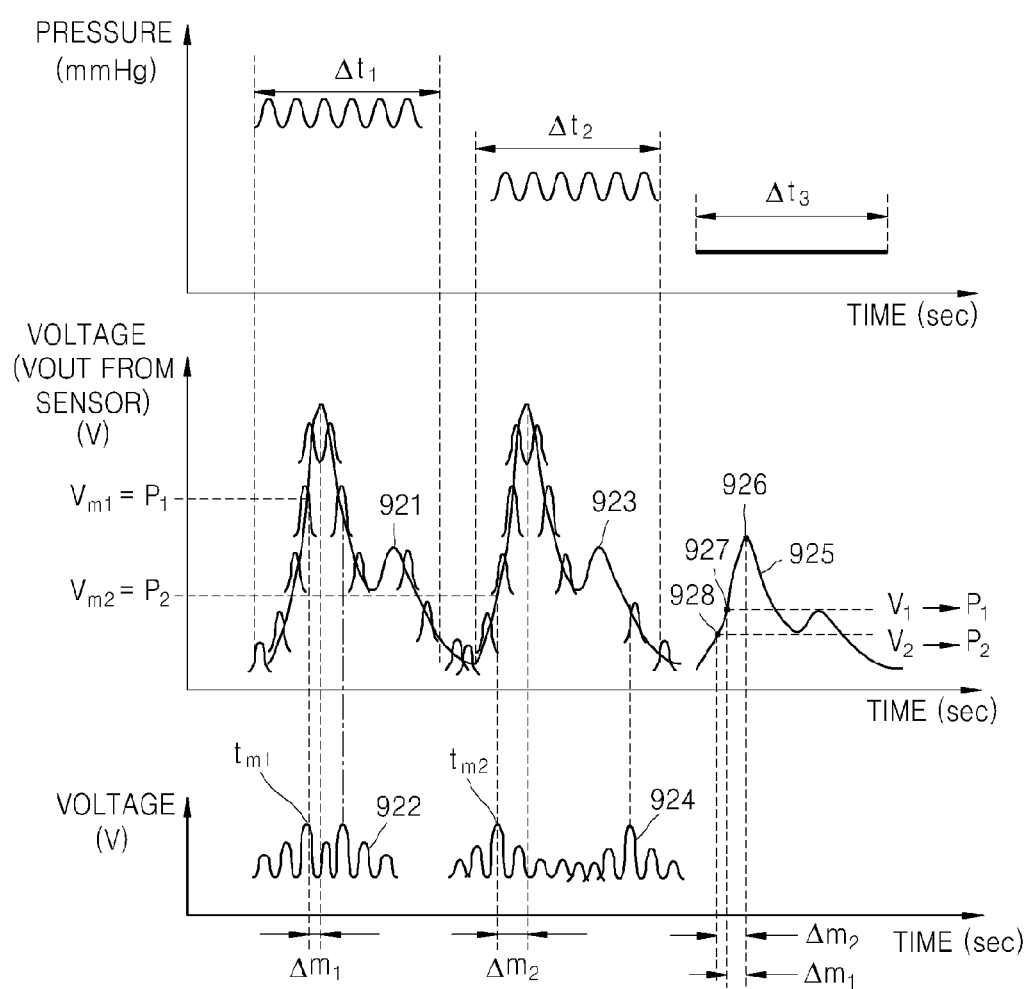
Figure 9D:
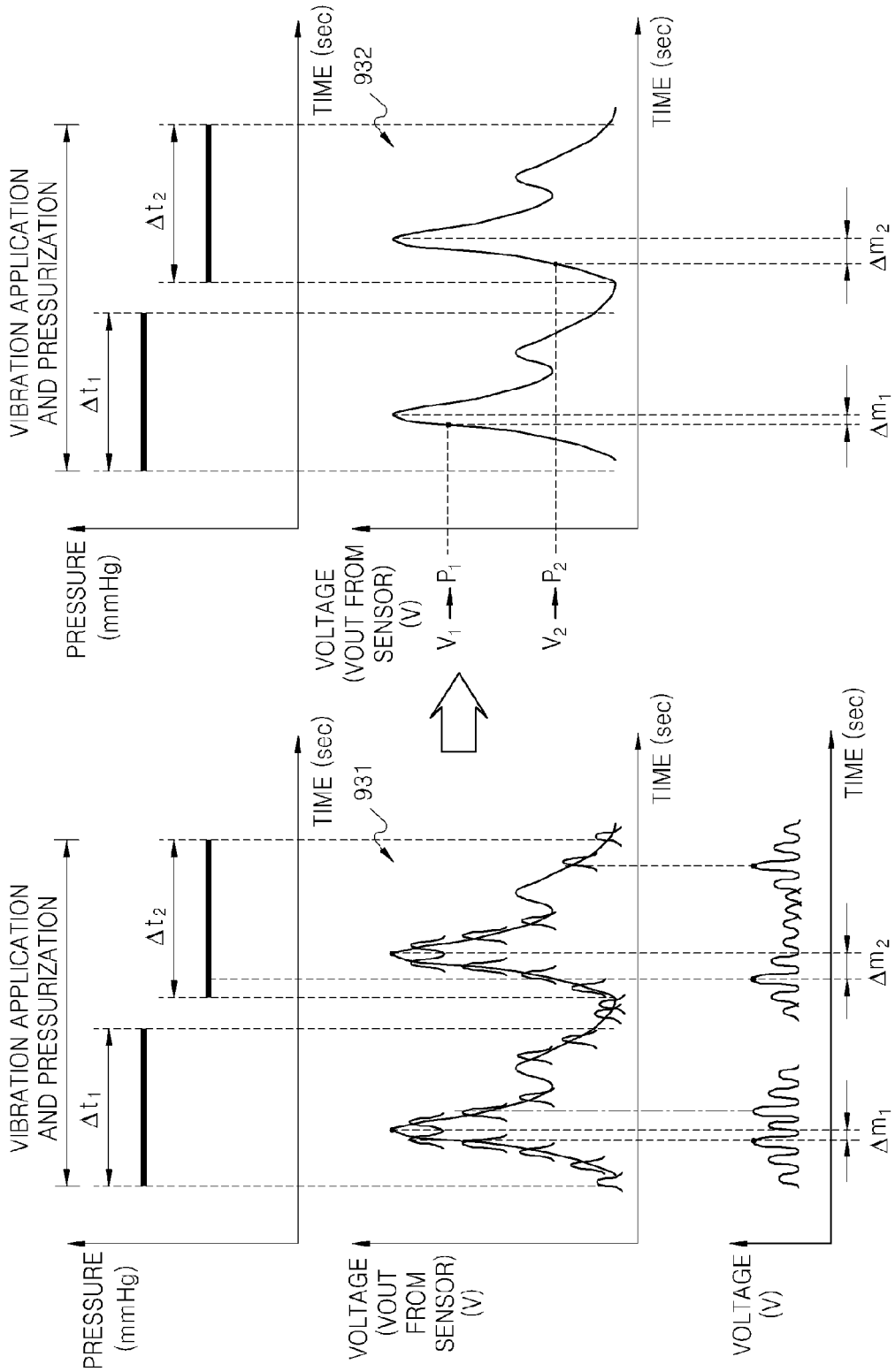

FIGS. 9A through 9D are graphs of voltage and pressure versus time showing determinations of voltages by the voltage determination unit 1522 according to one or more embodiments. Specifically, FIGS. 9A and 9B illustrate embodiments in which voltages are determined using a sphygmus wave sensed the wrist of a user to which the vibration application unit 13 applies a vibration and which the pressurizing unit 11 pressurizes. FIGS. 9C and 9D illustrate embodiments of determining voltages by using a sphygmus wave sensed while the pressurizing unit 11 pressurizes the wrist of the user with a vibrating pressure.

Referring to FIGS. 9A and 9C, as described above, the time difference calculation unit 1520 calculates a time difference $\Delta m_1$ by using the peaks of a sphygmus wave 901 or 921 and a high-frequency signal 902 or 922 which are sensed during a time $\Delta t_1$. The time difference calculation unit 1520 also calculates a time difference $\Delta m_2$ by using the peaks of a sphygmus wave 903 or 923 and a high-frequency signal 904 or 924 which are sensed during a time $\Delta t_2$. If respective periods of sphygmus waves sensed during the times $\Delta t_1$ and $\Delta t_2$ are not the same as a period of a sphygmus wave sensed during a time $\Delta t_3$, new time differences $\Delta m_x$ and $\Delta m_y$ are calculated using Equation 5, above.

Determination of voltages when the respective periods of the sphygmus waves sensed during the times $\Delta t_1$, $\Delta t_2$, and $\Delta t_3$ are substantially the same as one another will now be described. Since no vibration is applied to the wrist of a user, e.g., only a constant pressure is applied thereto during the time $\Delta t_3$, the sphygmus wave sensed during the time $\Delta t_3$ does not include vibration components.

At a point of time $t_{m1}$ when the high-frequency signal 902 or 922 peaks, a transmural pressure is 0, and the blood pressure within a blood vessel may be considered substantially equal to an external pressure applied to the blood vessel. Accordingly, a pressure $P_1$ corresponding to an output voltage $V_{m1}$ of a previously-calibrated sensor is an actual blood pressure at the point of time $t_{m1}$ when the high-frequency signal 902 or 922 peaks. Similarly, at a point of time $t_{m2}$ when the high-frequency signal 904 or 924 peaks, a transmural pressure is 0, and the blood pressure within the blood vessel may be considered equal to an external pressure. Accordingly, a pressure $P_2$ corresponding to an output voltage V of the previously-calibrated sensor is an actual blood pressure at the point of time $t_{m2}$ when the high-frequency signal 904 or 924 peaks.

The voltage determination unit 1522 determines voltages of points of time 907 and 908 or voltages 927 and 928, which differ from a point of time 906 or 926, when the sphygmus wave sensed during the time $\Delta t_3$ peaks, by the time differences $\Delta m_1$ and $\Delta m_2$. In other words, the voltage determination unit 1522 determines a voltage $V_1$ of the point of time 907 or 927 that differs from the point of time 906 or 926 by the time difference $\Delta m_1$, and determines a voltage $V_2$ of the point of time 908 or 928 that differs from the point of time 906 or 926 by the time difference $\Delta m_2$. The voltages $V_1$ and $V_2$ of the points of time 907 and 908 or the points of time 927 and 928 correspond to the pressures $P_1$ and $P_2$ corresponding to the points of time $t_{m1}$ and $t_{m2}$ when the high-frequency signal 902 or 922 and the frequency signal 904 or 924 peak. The voltages $V_1$ and $V_2$ correspond to actual blood pressures. Accordingly, the blood pressure calculation unit 1523 calculates the blood pressure of the wrist of the user by using the voltages $V_1$ and $V_2$ of the points of time 907 and 908 or the points of time 927 and 928.

Determination of voltages when the respective periods of the sphygmus waves sensed during the times $\Delta t_1$, $\Delta t_2$, and $\Delta t_3$ are different from one another, and will now be described in greater detail. In an embodiment, voltages are determined using the new time differences $\Delta m_x$ and $\Delta m_y$ calculated using Equation 5, discussed above. In other words, the voltage determination unit 1521 determines a voltage $V_1$ of a point of time corresponding to the time difference $\Delta m_x$ in the sphygmus wave sensed during the time $\Delta t_3$, and a voltage $V_2$ of a point of time corresponding to the time difference $\Delta m_y$ in the sensed sphygmus wave.

Referring now to FIGS. 9B and 9D, in contrast with FIGS. 9A and 9C, additional application of a constant pressure does not occur. Accordingly, determination of voltages in a sphygmus wave sensed during the time $\Delta t_3$, illustrated in FIGS. 9A and 9B, may not occur. Therefore, in the embodiments illustrated in FIGS. 9B and 9D, low-frequency signals 912 and 932 extracted by the second filtering unit 1512 by using sphygmus waves 911 and 931, respectively, each sensed during the times $\Delta t_1$ and $\Delta t_2$, are used. The time difference calculation unit 1520 calculates time differences $\Delta m_1$ and $\Delta m_2$ from each of the sphygmus wave 911 and 931 sensed during the times $\Delta t_1$ and $\Delta t2$. The second filtering unit 1512 extracts the low-frequency signal 912 and 932 by passing the sensed sphygmus waves 911 and 931 through an LPF. The voltage determination unit 1522 determines voltages $V_1$ and $V_2$ of points of time corresponding to the time differences $\Delta m_1$ and $\Delta m_2$ by using the time differences $\Delta m_1$ and $\Delta m_2$ and each of the low-frequency signals 912 and 932. In the embodiments illustrated in FIGS. 9B and 9D as described above, since only the sphygmus waves 911 and 931 each sensed during the times $\Delta t_1$ and $\Delta t_2$ are used, new time differences $\Delta m_x$ and $\Delta m_y$ as in the embodiments of FIGS. 9A and 9C do not need to be calculated.

The blood pressure calculation unit 1523 calculates blood pressures by using the voltages determined by the voltage determination unit 1522. First, the blood pressure calculation unit 1523 obtains the coefficients α and β of Equation 4 and the determined voltages. Thereafter, the blood pressure calculation unit 1523 calculates the blood pressures by using Equation 4 and either the sphygmus wave sensed by the sensing unit 14 or the low-frequency signal extracted by the second filtering unit 1512. The first blood pressure estimation unit 1521 estimates the calculated blood pressures as the actual blood pressures of the wrist of the user.

Specifically, the voltages determined by the voltage determination unit 1522 are voltages corresponding to points of time when the transmural pressure is 0. Thus, pressures corresponding to the determined voltages are substantially the same as the actual blood pressures of the wrist of the user. The pressures corresponding to the determined voltages may be obtained using Equation 2, above.

When the coefficients α and β of Equation 4 (above) are known, a relationship between a voltage and an actual blood pressure may be ascertained using voltages corresponding to the sphygmus wave sensed by the sensing unit 14 or the low-frequency signal extracted by the second filtering unit 1512. Therefore, the voltages determined by the voltage determination unit 1522 are first used to obtain the coefficients α and β of Equation 4. In this case, Equation 6, below, may be used.

$$BP_1 = P_1 = \alpha \cdot V_1 + \beta,$$

$$BP_2 = P_2 = \alpha \cdot V_2 + \beta \qquad \text{Equation 6:}$$

The upper equation in Equation 6 is obtained by substituting the voltage $V_1$, determined by the voltage determination unit 1522 and the pressure $P_1$ corresponding to the voltage $V_1$, into Equation 4. The pressure $P_1$ is substituted into the blood pressure BP of Equation 4 because the voltage $V_1$ is a voltage determined at a point of time when the transmural pressure is 0. Similarly, the lower equation in Equation 6 is obtained by substituting the voltage $V_2$, determined by the voltage determination unit 1522 and the pressure $P_2$ corresponding to the voltage $V_2$, into Equation 4. Since $V_1$, $V_2$, $P_1$ and $P_2$ in Equation 6 are all known, the coefficients α and β may be calculated by combining the upper and lower equations in Equation 6.

When the coefficients α and β have been calculated using Equation 6, as discussed above, the blood pressure calculation unit 1523 calculates the actual blood pressures of the wrist of the user by using Equation 4. Since the sphygmus wave sensed by the sensing unit 14 or the low-frequency signal extracted by the second filtering unit 1512 is a voltage signal, voltages corresponding to the sensed sphygmus wave or the extracted low-frequency signal may be known. The blood pressure calculation unit 1523 substitutes the voltages corresponding to the sensed sphygmus wave or the extracted low-frequency signal into Equation 4. Since the coefficients α and β and the voltage V of Equation 4 are known, the blood pressure calculation unit 1523 calculates blood pressures BPs according to the voltage V. These calculated blood pressures BPs correspond to the actual blood pressures of the body part, e.g., the wrist, of the user.

Figure 10:
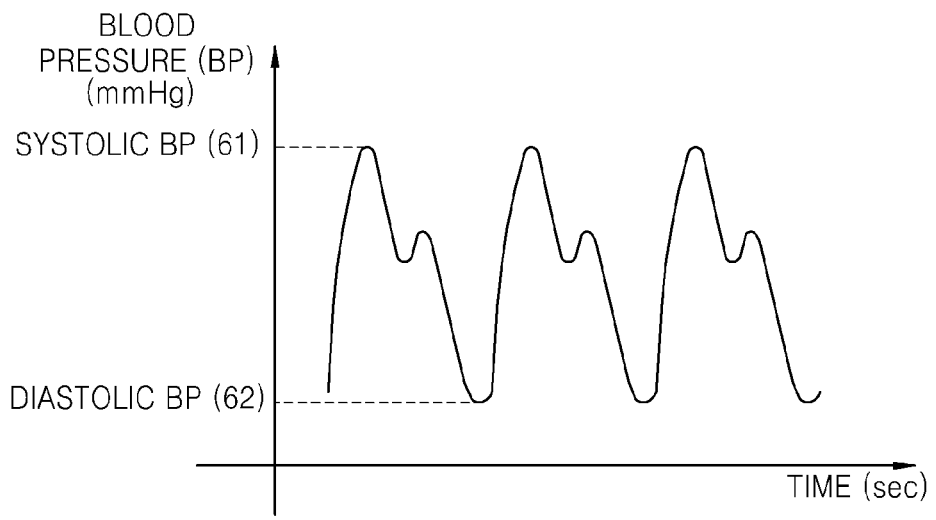
FIG. 10 is a graph of blood pressure versus time showing blood pressures estimated by the blood pressure estimation unit illustrated in FIG. 2.

FIG. 10 is a graph of blood pressure showing blood pressures estimated by the blood pressure estimation unit 152 illustrated in FIG. 2. Referring to FIG. 10, the estimated blood pressures BP are illustrated in the waveforms of BP according to time (t). The BPs estimated by the blood pressure estimation unit 152 are the BPs calculated by the blood pressure calculation unit 1523. A maximum BP from among the BPs estimated by the blood pressure estimation unit 152 may be estimated as a systolic BP 1001, and a minimum BP from among the estimated BPs may be estimated as a diastolic BP 1002.

Referring again to FIG. 2, the second blood pressure estimation unit 1524 includes the characteristic ratio calculation unit 1525 and the blood pressure determination unit 1526. If the user selects the characteristic ratio application mode, the second blood pressure estimation unit 1524 estimates blood pressures by using the blood pressure characteristic ratio of the user. The estimated BPs are transmitted to the user interface unit 17, and the user interface unit 17 outputs the transmitted blood pressures to the user. Hereinafter, the characteristic ratio calculation unit 1525 and the blood pressure determination unit 1526 will be described as operating in the characteristic ratio application mode.

In one or more embodiments, the characteristic ratio calculation unit 1525 calculates the blood pressure characteristic ratio of the user by using a sphygmus wave sensed while a constantly-increasing or decreasing pressure is applied and by using the voltages estimated by the first blood pressure estimation unit 1521. Specifically, the high-frequency signal and the low-frequency signal extracted by passing the sphygmus wave sensed by the sensing unit 14 through the filtering unit 151 and the systolic blood pressure and the diastolic blood pressure from among the estimated blood pressures are used. The systolic blood pressure is the maximum blood pressure from among the estimated blood pressures, and the diastolic blood pressure is the minimum.

In embodiments, the characteristic ratio calculation unit 1525 does not operate only in the characteristic ratio application mode, as discussed above, but also operates in the blood pressure calculation mode. In other words, when the first blood pressure estimation unit 1521 estimates blood pressures according to the blood pressure calculation mode, the first blood pressure estimation unit 1521 transmits the maximum and minimum blood pressures from among the blood pressures estimated by the characteristic ratio calculation unit 1525, and the characteristic ratio calculation unit 1525 calculates the blood pressure characteristic ratio of the user.

The blood pressure determination unit 1526 determines the blood pressures of the wrist of the user based on a sphygmus wave sensed from the wrist that is newly pressurized with a continuously-increasing or decreasing pressure and by using the blood pressure characteristic ratio of the user. In other words, when the user selects the characteristic ratio application mode, the blood pressures of the wrist are determined using the previously-calculated and stored blood pressure characteristic ratio of the user and the sphygmus wave newly sensed by the sensing unit 14. The blood pressures of the wrist are determined using an oscillometric technique, for example. Since the blood pressures determined by the blood pressure determination unit 1526 according to the characteristic ratio application mode as described above are based on the blood pressure characteristic ratio, which is based on the actual blood pressures of the user, an accuracy of the determined blood pressures is substantially improved, as compared to using a statistics-based blood pressure characteristic ratio.

Referring again to FIG. 1, the storage unit 16 stores results of operations and/or processes performed in the processor 15, and the processor 15 reads information from the storage unit 16. For example, when the characteristic ratio calculation unit 1525 calculates a blood pressure characteristic ratio, the storage unit 16 stores the blood pressure characteristic ratio. Thereafter, if the user selects the characteristic ratio application mode, the blood pressure of the user is determined using the stored blood pressure characteristic ratio.

The user interface unit 17 receives information from the user and outputs information, such as blood pressures, for example, to the user. The outputted blood pressures denote the blood pressures estimated by the blood pressure estimation unit 152. The user interface unit 17 obtains information from the user using any type of information input device or method, such as a keyboard, a mouse, a touch screen or speech recognition, for example, but not being limited thereto. Whether to use the blood pressure calculation mode or the characteristic ratio application mode is determined by the user inputting a desired mode to the user interface unit 17. Examples of the user interface unit 17 may include a device which displays visual information, e.g., a display such as a liquid crystal display ("LCD") screen, a light-emitting diode ("LED") display or a division display device, or any device which provides the user with auditory information (such as, speakers, for example).

Figure 11:
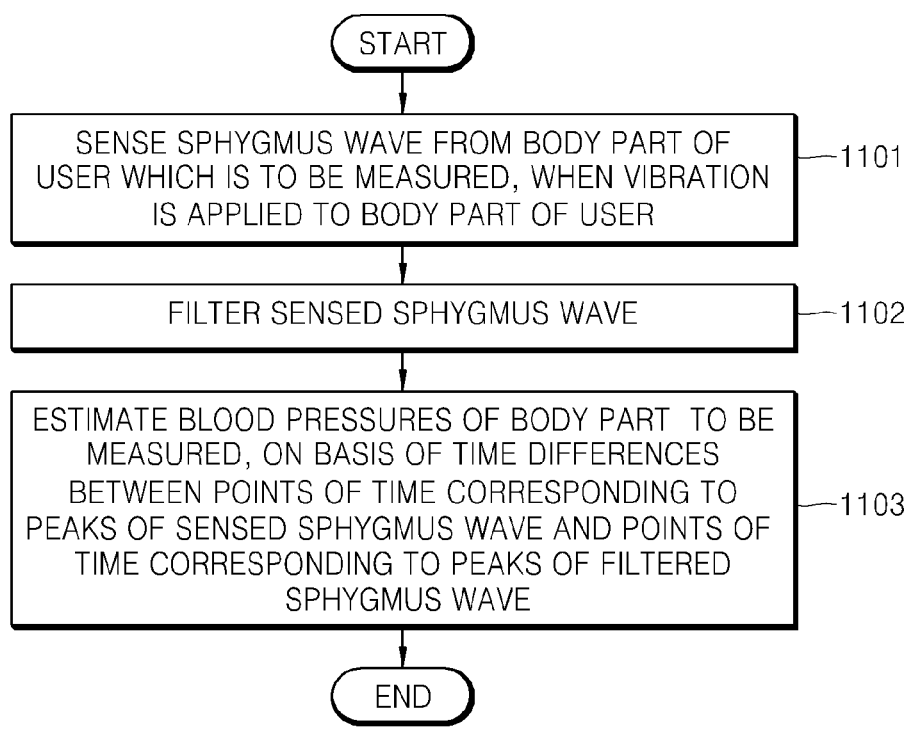
FIG. 11 is a flowchart of a method of estimating blood pressure according to an embodiment.

FIG. 11 is a flowchart of a method of estimating blood pressure according to an embodiment. Referring to FIG. 11, the blood pressure estimation method includes operations performed sequentially in the blood pressure estimating apparatus 1 of FIG. 1. Therefore, although not explicitly described in the current embodiment, the content described above in connection with the blood pressure estimating apparatus 1 of FIG. 1 also applies to embodiments of the method described herein.

In operation 1101, the sensing unit 14 (FIG. 1) senses a sphygmus wave from a body part of a user, which is to be measured, while vibration is applied to the body part of the user. The body part of the user corresponds to a part of the body from which blood pressure may be measured, such as the wrist, for example. The applied vibration denotes a vibration applied by the vibration application unit 13 or a vibrating pressure applied by the pressurizing unit 11, as described in greater detail above.

In operation 1102, the filtering unit 151 filters the sphygmus wave sensed by the sensing unit 14.

In operating 1103, the blood pressure estimation unit 152 estimates blood pressures of the body part to be measured, based on time differences between points of time corresponding to peaks of the sensed sphygmus wave and points of time corresponding to peaks of the filtered sphygmus wave.

Figure 12:
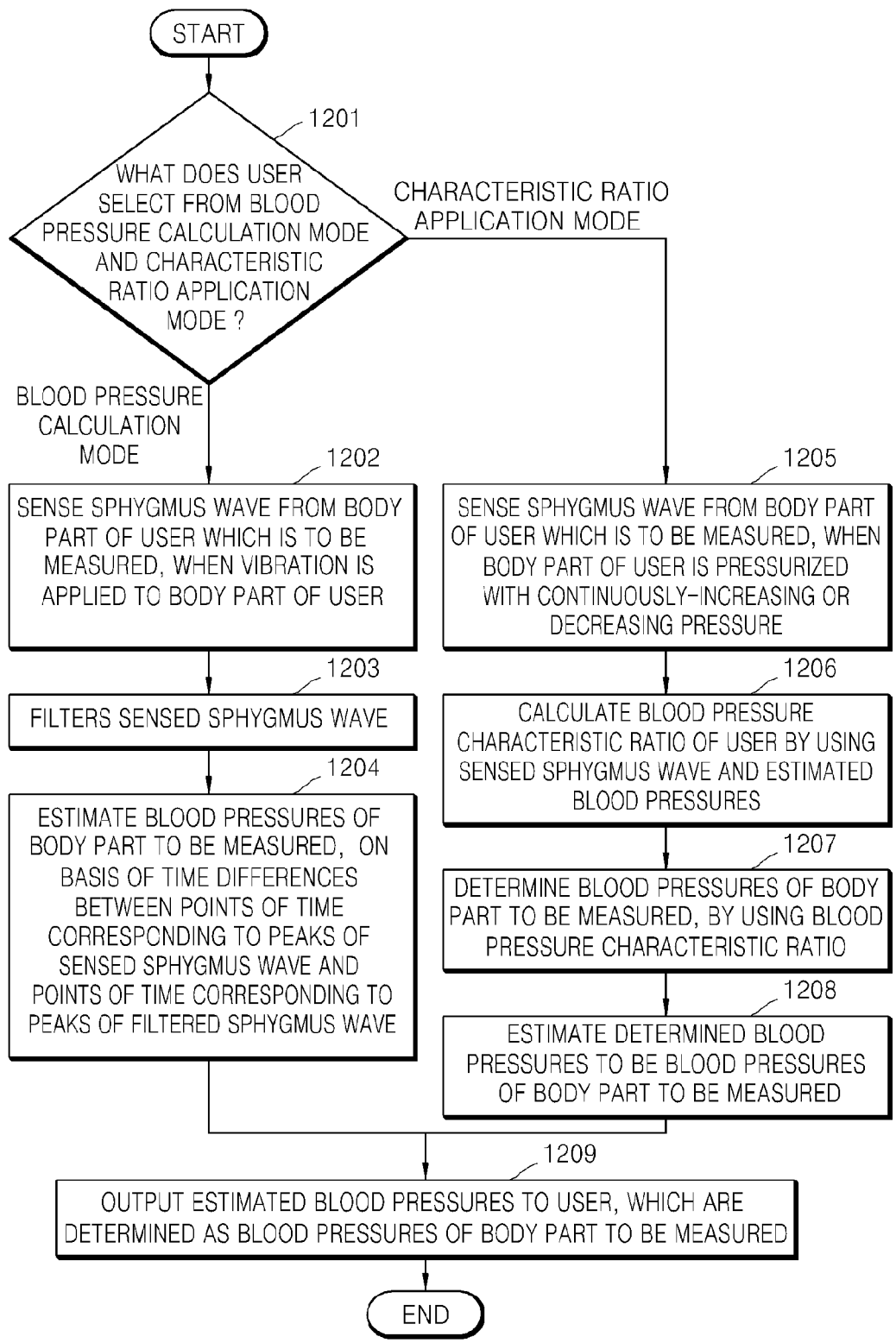
FIG. 12 is a flowchart of a method of estimating blood pressure in a blood pressure calculation mode or a characteristic ratio application mode according to an embodiment.

FIG. 12 is a flowchart of an embodiment of a method of estimating blood pressure in a blood pressure calculation mode or a characteristic ratio application mode. Referring to FIG. 12, the blood pressure estimation method includes operations, which may be performed sequentially, in the blood pressure estimating apparatus 1 in FIG. 1. Therefore, although not explicitly described in the current embodiment, an embodiment if using the above-described blood pressure estimating apparatus 1 in FIG. 1 also applies to the method of the embodiment described hereinafter.

In operation 1201, the use of either the blood pressure calculation mode or the characteristic ratio application mode is selected by a user inputting a desired mode to the user interface unit 17.

In operation 1202, when the blood pressure calculation mode is selected, the sensing unit 14 senses a sphygmus wave from a body part of the user, which is to be measured, when vibration is applied to the body part of the user. The body part of the user corresponds to a part of the body from which blood pressure may be measured, such as the wrist, for example. The applied vibration denotes a vibration applied by the vibration application unit 13 or a vibrating pressure applied by the pressurizing unit 11.

In operation 1203, in the blood pressure calculation mode, the filtering unit 151 filters the sphygmus wave sensed by the sensing unit 14.

In operation 1204, in the blood pressure calculation mode, the first blood pressure estimation unit 1521 estimates blood pressures of the body part to be measured, based on time differences between points of time corresponding to peaks of the sensed sphygmus wave and points of time corresponding to peaks of the filtered sphygmus wave.

In operation 1205, when the characteristic ratio application mode is selected, the sensing unit 14 senses a sphygmus wave from the body part of the user, when the body part of the user is pressurized with a continuously-increasing or decreasing pressure.

In operation 1206, in the characteristic ratio application mode, the characteristic ratio calculation unit 1525 calculates a blood pressure characteristic ratio of the user by using the sphygmus wave sensed when the body part of the user is pressurized with the continuously-increasing or decreasing pressure and by using blood pressures estimated by the first blood pressure estimation unit 1521.

In operation 1207, in the characteristic ratio application mode, the blood pressure determination unit 1526 determines blood pressures of the wrist by using the blood pressure characteristic ratio.

In operation 1208, in the characteristic ratio application mode, the second blood pressure estimation unit 1524 estimates the determined blood pressures to be the blood pressures of the wrist.

In operation 1209, the user interface unit 17 outputs the estimated blood pressures, which are as the blood pressures of the wrist, to the user.

Figure 13:
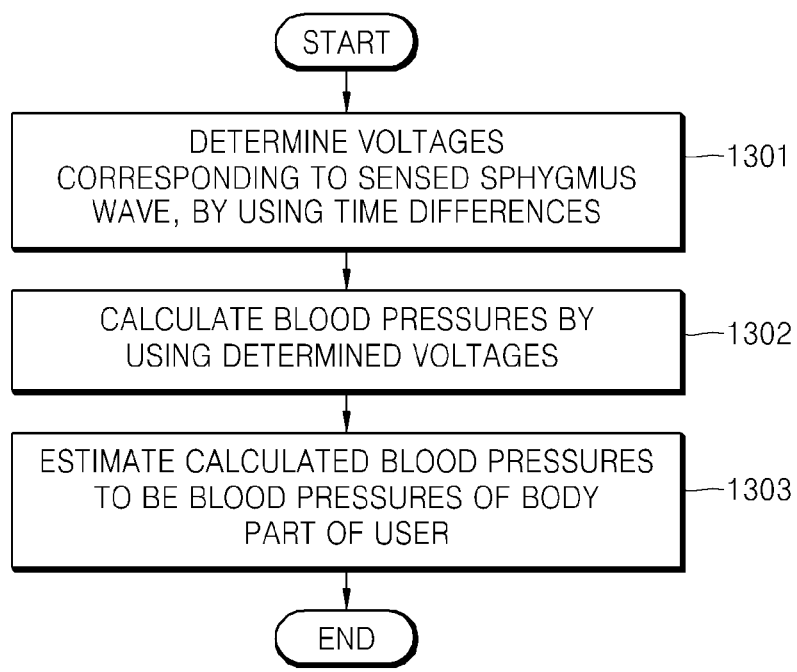
FIG. 13 is a flowchart of an operation of estimating blood pressures of a body part to be measured, on the basis of time differences between points of time corresponding to peaks of a sensed sphygmus wave and points of time corresponding to peaks of a filtered sphygmus wave, included in the method illustrated in FIG. 11.

FIG. 13 is a flowchart of an embodiment of operation 1103 illustrated in FIG. 11. Referring to FIG. 13, operation 1103 includes operations, which may be performed sequentially, in the blood pressure estimating apparatus 1 in FIG. 1. Therefore, although not explicitly described hereinafter, the content described in greater detail above with respect to the blood pressure estimating apparatus 1 in FIG. 1 also applies to embodiments of the method described below.

In operation 1301, according to an embodiment, the voltage determination unit 1522 determines voltages corresponding to a sphygmus wave sensed while application of vibration is interrupted, e.g., stopped, by using the time differences described above. The interruption of the application of vibration denotes that the vibration application unit 13 stops applying vibration and only the pressurizing unit 11 applies a constant pressure. According to another embodiment, the voltage determination unit 1522 determines the voltages corresponding to a sphygmus wave sensed while the body part of the user is being pressurized with a constant pressure, by using the abovementioned time differences. The pressurization of the body part of the user with the constant pressure denotes that the pressurizing unit 11 pressurizes the body part of the user with a vibrating pressure and then pressurizes the body part of the user with the constant pressure having a constant value. According to another embodiment, the voltage determination unit 1522 determines the voltages corresponding to an extracted low-frequency signal, by using the time differences. The extracted low-frequency signal denotes the low-frequency signal extracted by the second filtering unit 1512. The pressure determination unit 1522 transmits the determined voltages to the blood pressure calculation unit 1523.

In operation 1302, the blood pressure calculation unit 1523 calculates blood pressures by using the voltages determined by the voltage determination unit 1522. Specifically, the blood pressure calculation unit 1523 obtains the coefficients $\alpha$ and $\beta$ of Equation 4 (above) by using Equation 4 and the determined voltages. The blood pressure calculation unit 1523 calculates the blood pressures by using Equation 4 and either the sphygmus wave sensed by the sensing unit 14 or the low-frequency signal extracted by the second filtering unit 1512.

In operation 1303, the blood pressure estimation unit 152 estimates the blood pressures (e.g., the calculated blood pressures) of the body part of the user.

As described herein, according to one or more of embodiments, blood pressure is accurately measured, since a statistical characteristic ratio, which may have an error due differences in race, gender and/or age, for example, of a particular user, is not used. Also, the blood pressure may be continuously measured in the embodiments described herein.

The embodiments of the present invention can be written as computer programs and can be implemented in specific- or general-use computers that execute the computer programs using a computer readable recording medium. Data used in the above-described embodiments can be recorded on the medium in various ways. Non-limiting examples of the computer readable recording medium include magnetic storage media, such as read only memory ("ROM"), floppy disks and hard disks, for example, as well as optical recording media, such as compact disc-ROMs ("CD-ROMs") or digital versatile discs ("DVDs"), for example, but not being limited thereto.

It will be understood that the embodiments described herein will be considered in a descriptive sense only, and not for purposes of limitation. Descriptions of aspects within each embodiment should be considered as available for other similar aspects in other embodiments.

While the general inventive concept disclosed herein has been particularly shown and described with reference to exemplary embodiments thereof, it will be understood by those of ordinary skill in the art that various changes in form and details may be made therein without departing from the spirit or scope of the present invention as defined by the following claims.

What is claimed is:

1. A method for estimating blood pressure, the method comprising:
   sensing a sphygmus wave at a body part of a user to which vibration is applied for a predetermined time to generate a sensed sphygmus wave;
   filtering the sensed sphygmus wave to generate a filtered sphygmus wave; and
   estimating blood pressure of the user based on time differences between peaks of the sensed sphygmus wave and peaks of the filtered sphygmus wave.

2. The method of claim 1, wherein
   the filtering the sensed sphygmus wave comprises filtering out a high-frequency signal having a frequency of the vibration from the sensed sphygmus wave to generate a filtered-out high-frequency signal, and
   the estimating the blood pressure comprises estimating the blood pressure of the body part based on time differences between points of time corresponding to the peaks of the sensed sphygmus wave and points of time corresponding to peaks of the filtered-out high-frequency signal.

3. The method of claim 1, further comprising controlling application of the vibration to the body part and pressurization of the body part with different constant pressures,
   wherein the sensing the sphygmus wave comprises sensing sphygmus waves from the body part when the body part subjected to the vibration and pressurized with the different constant pressures.

4. The method of claim 3, wherein
   the sensing the sphygmus wave further comprises sensing the sphygmus wave at the body part when application of the vibration to the body part is stopped after the predetermined time, and
   the estimating the blood pressure based on the time differences between the peaks of the sensed sphygmus wave and the peaks of the filtered sphygmus wave comprises estimating the blood pressures of the body part based on the time differences and a result of the sensing the sphygmus wave at the body part when application of the vibration to the body part is stopped after the predetermined time.

5. The method of claim 4, wherein the estimating of the blood pressure based on the time differences and the result of the sensing the sphygmus wave at the body part when application of the vibration to the body part is stopped after the predetermined time comprises:
   determining voltages corresponding to the sphygmus wave sensed when the application of the vibration to the body part is stopped after the predetermined time to generate determined voltages; and
   pressure of the body part by calculating blood pressures based on the determined voltages.

6. The method of claim 2, wherein
   the filtering the sensed sphygmus wave further comprises filtering out a low-frequency signal having a frequency lower than the frequency of the vibration from the sensed sphygmus wave,
   the estimating the blood pressure further comprises:
   determining voltages corresponding to a filtered-out low-frequency signal based on the time differences; and
   calculating the blood pressure based on the determined voltages, and
   the blood pressure of the body part is estimated based on the calculated blood pressures.

7. The method of claim 1, further comprising pressurizing the body part with different vibrating pressures,
   wherein the sensing the sphygmus wave comprises sensing sphygmus waves at the body part which is pressurized with the different vibrating pressures.

8. The method of claim 7, further comprising pressurizing the body part with a constant pressure, wherein
   the sensing the sphygmus wave further comprises sensing sphygmus waves at the body part which is pressurized with the constant pressures, and
   the estimating the blood pressure comprises estimating blood pressures of the body part based on the time differences and the sphygmus waves sensed when the body part is pressurized with the constant pressure.

9. The method of claim 8, wherein
   the estimating the blood pressures further comprises:
   determining voltages corresponding to the sphygmus waves sensed when the body part is pressurized with the constant pressure based on the time differences to generate determined voltages; and
   calculating blood pressures based on the determined voltages, and
   the blood pressure of the body part is estimated based on the calculated blood pressures.

10. The method of claim 7, wherein
    the filtering the sensed sphygmus wave further comprises filtering out a low-frequency signal having a frequency lower than a frequency of the vibration from the sensed sphygmus wave to generate a filtered-out low-frequency signal,
    the estimating the blood pressures further comprises:
    determining voltages corresponding to the filtered-out low-frequency signal, based on the time differences, to generate determined voltages; and
    calculating blood pressures based on the determined voltages, and
    the blood pressure of the body part is estimated based on the calculated blood pressures.

11. The method of claim 1, wherein
    the sensing the sphygmus wave is performed when the body part is pressurized with one of a constantly increasing pressure and a constantly decreasing pressure,
    the estimating the blood pressure comprises:
    calculating a blood pressure characteristic ratio of the user based on the sphygmus wave sensed when the body part is pressurized with the one of the constantly increasing pressure and the constantly decreasing pressure and the estimated blood pressure; and
    determining the blood pressure of the body part based on the blood pressure characteristic ratio to generate determined blood pressures, and
    the estimated blood pressures of the body part are based on the determined blood pressures.

12. A non-transitory computer program product comprising a computer readable computer program code for executing a method of estimating blood pressure and instructions for causing a computer to implement the method, the method comprising:
    sensing a sphygmus wave at a body part of a user to which vibration is applied to generate a sensed sphygmus wave by a sensing unit;
    filtering the sensed sphygmus wave to generate a filtered sphygmus wave by a filtering unit; and
    estimating blood pressure of the user based on time differences between peaks of the sensed sphygmus wave and peaks of the filtered sphygmus wave by a blood pressure estimation unit.

13. An apparatus for estimating blood pressure, the apparatus comprising:

a sensing unit which senses a sphygmus wave at a body part of a user to which vibration is applied for a predetermined time to generate a sensed sphygmus wave;

a filtering unit which filters the sensed sphygmus wave to generate a filtered sphygmus wave;

a blood pressure estimation unit which estimates blood pressure of the user based on time differences between peaks of the sensed sphygmus wave and peaks of the filtered sphygmus wave; and a user interface unit which outputs estimated blood pressures.

14. The apparatus of claim 13, wherein:

the filtering unit filters out a high-frequency signal having a frequency of the vibration from the sphygmus wave to generate a filtered-out high-frequency signal; and the blood pressure estimation unit estimates the blood pressure of the body part based on time differences between points of time corresponding to the peaks of the sensed sphygmus wave and points of time corresponding to peaks of the filtered-out high-frequency signal.

15. The apparatus of claim 13, further comprising a control unit which controls application of the vibration to the body part and pressurization of the body part with different constant pressures, wherein the sensing unit senses the sphygmus wave from the body part when the body part is subjected to the vibration and is pressurized with the different constant pressures.

16. The apparatus of claim 15, wherein the sensing unit further senses the sphygmus wave from the body when application of the vibration to the body part is stopped after the predetermined time, and the blood pressure estimation unit estimates the blood pressure of the body part based on the time differences and the sphygmus wave further sensed when the vibration to the body part is stopped after the predetermined time.

17. The apparatus of claim 14, wherein the filtering unit further filters out a low-frequency signal having a frequency lower than the frequency of the vibration from the sphygmus wave to generate a filtered-out low-frequency signal, the blood pressure estimation unit comprises:

a voltage determination unit which determines voltages corresponding to the filtered-out low-frequency signal based on the time differences to generate determined voltages; and a blood pressure calculation unit calculates blood pressures based on the determined voltages; and the blood pressure of the body part is estimated based on the calculated blood pressures.

18. The apparatus of claim 13, further comprising a control unit which pressurizes the body part with different vibrating pressures, wherein the sensing unit senses sphygmus waves from the body part when the body part is pressurized with the different vibrating pressures.

19. The apparatus of claim 18, wherein the control unit further pressurizes the body part with a constant pressure, the sensing unit senses a sphygmus wave from the body part when the body part is pressurized with the constant pressure, and the blood pressure estimation unit estimates blood pressures of the body part based on the time differences and the sphygmus wave sensed when the body part is pressurized with the constant pressure.

20. The apparatus of claim 15, wherein the filtering unit filters out a low-frequency signal having a frequency lower than a frequency of the vibration from the sensed sphygmus wave to generate a filtered-out low-frequency signal, the blood pressure estimation unit estimates of the blood pressures by determining voltages corresponding to the filtered-out low-frequency signal based on the time differences to generate determined voltages, the blood pressure estimation unit calculates the blood pressure based on the determined voltages, and the blood pressure of the body part is estimated based on the calculated blood pressures.

* * * * *